US010746718B2

(12) United States Patent
Zimbron

(10) Patent No.: US 10,746,718 B2
(45) Date of Patent: Aug. 18, 2020

(54) ESTABLISHMENT OF CONTAMINANT DEGRADATION RATES IN SOILS USING TEMPERATURE GRADIENTS

(71) Applicant: E-Flux, LLC, Fort Collins, CO (US)

(72) Inventor: Julio Zimbron, Fort Collins, CO (US)

(73) Assignee: E-Flux, LLC, Fort Collins, CO (US)

( * ) Notice: Subject to any disclaimer, the term of this patent is extended or adjusted under 35 U.S.C. 154(b) by 534 days.

(21) Appl. No.: 15/137,958

(22) Filed: Apr. 25, 2016

(65) Prior Publication Data

US 2017/0023539 A1 Jan. 26, 2017

Related U.S. Application Data

(60) Provisional application No. 62/151,564, filed on Apr. 23, 2015, provisional application No. 62/158,823, filed on May 8, 2015, provisional application No. 62/159,445, filed on May 11, 2015.

(51) Int. Cl.
*G01N 33/24* (2006.01)
*G01N 25/48* (2006.01)

(52) U.S. Cl.
CPC ......... *G01N 33/24* (2013.01); *G01N 25/4846* (2013.01); *G01N 2033/243* (2013.01)

(58) Field of Classification Search
None
See application file for complete search history.

(56) References Cited

U.S. PATENT DOCUMENTS

| | | | |
|---|---|---|---|
| 2007/0131411 | A1 | 6/2007 | Vinegar et al. |
| 2008/0099569 | A1 | 5/2008 | Plumpton et al. |
| 2013/0260441 | A1 | 10/2013 | Fowler |
| 2015/0120194 | A1 | 4/2015 | Chen |

OTHER PUBLICATIONS

Popiel, Czeslaw Oleskowicz, Janusz Wojtkowiak, and Beata Biernacka. "Measurements of temperature distribution in ground." Experimental thermal and fluid science 25.5 (2001): 301-309.*
Larter, Steve, et al. "The controls on the composition of biodegraded oils in the deep subsurface: Part II—Geological controls on subsurface biodegradation fluxes and constraints on reservoir-fluid property prediction1." AAPG bulletin 90.6 (2006): 921-938.*
Jeong, Hoon Y., et al. "Abiotic reductive dechlorination of cis-dichloroethylene by Fe species formed during iron- or sulfate-reduction." Environmental science & technology 45.12 (2011):5186-5194.
Godbout, S., V.R. Phillips, and R.W. Sneath. Passive Flux Samplers to measure Nitrous Oxide and Methane Emissions from Agricultural Sources, Part 1: Adsorbent Selection. Biosystems Engineering (2006) 94 (4), 587-596. doi:10.1016/j.biosystemseng. 2006.04.14.
Godbout, S., V.R. Phillips, and R.W. Sneath. Passive Flux Samplers to measure Nitrous Oxide and Methane Emissions from Agricultural Sources, Part 2: Desorption Improvements. Biosystems Engineering (2006) 95 (1), 1-6 . doi:10.1016/j.biosystemseng. 2006.05.07.
Hutchinson, G.L. and Livingston, G.P. 2002 Soil—atmosphere gas exchange. In Dane, J.H. and Topp, G.C. (Eds.), Methods of Soil Analysis, Part 4, SSSA Book Series 5, SSSA, Madison, WI, USA, pp. 1159-1182.
Lundegard, Paul D., and Paul C. Johnson. 2006. Source zone natural attenuation at petroleum hydrocarbon spill sites II: application to a former oil field. Groundwater Monitoring & Remediation 26.4: 93-106.
Molins, S., K.U. Mayer, R.T. Amos, and B.A. Bekins. 2010. Vadose zone attenuation of organic compounds at a crude oil spill site—Interactions between biogeochemical reactions and multicomponent gas transport. Journal of Contaminant Hydrology. 112:15-29. doi: 10.1016/j.jconhyd, Sep. 2, 2009.
Essaid, H.I., B.A. Bekins, W.N. Herkelrath, and G.N. Delin. 2011. Crude Oil at the Bemidji Site: 25 Years of Monitoring, Modeling, and Understanding. Groundwater. 49:706-726. doi:10.1111/j.1745-6584.2009.00654.x.
Amos, R.T., K.U. Mayer, B.A. Bekins, G.N. Delin, and R.L. Williams. 2005. Use of dissolved and vapor-phase gases to investigate methanogenic degradation of petroleum hydrocarbon contamination in the subsurface. Water Resources Research. 41:W02001. doi:10.1029/2004WR003433.
Bravo, H.R., F. Jiang, and R.J. Hunt. 2002. Using groundwater temperature data to constrain parameter estimation in a groundwater flow model of a wetland system. Water Resources Research. 38:1153 doi:10.1029/2000WR000172.
Bristow, K.L. 1997. Measurement of thermal properties and water content of unsaturated sandy soil using dual-probe heat-pulse probes. Agricultural and Forest Meteorology. 89:75-84. doi:10.1016/S0168-1923(97)00065-8.
Carson, J.E., and H. Moses. 1963. The Annual and Diurnal Heat-Exchange Cycles in Upper Layers of Soil. Journal of Applied Meteorology. 2:397-406. doi:10.1175/1520-0450(1963)002.
Chiasson, A.D. 1999. Advances in Modeling of Ground-Source Heat Pump Systems. Master of Science thesis, Oklahoma State University.
Dillard, L.A., H.I. Essaid, and W.N. Herkelrath. 1997. Multiphase flow modeling of a crude-oil spill site with a bimodal permeability distribution. Water Resources Research. 33:1617-1632. doi:10.1029/97WR00857.

(Continued)

*Primary Examiner* — G Steven Vanni
(74) *Attorney, Agent, or Firm* — Davis, Brown, Koehn, Shors & Roberts, P.C.; Matthew Warner-Blankenship

(57) ABSTRACT

The disclosed apparatus, systems and methods relate to estimating the rate of biodegradation of contaminants in the ground by measuring thermal gradients in the vadose zone where heat is produced by biodegradation reactions, and averaging over a full seasonal period, such as one year or one seasonal cycle, in which the groundwater temperatures and surface temperatures vary in a cyclical manner. Exemplary embodiments correct for the delay required by the heat being produced in the ground to reach the locations where the temperature gradients are measured, and also cancel out the signal noise caused by the changing surface and groundwater temperatures. In further embodiments, a mathematical model is provided to test the validity of the invention on two example sites.

14 Claims, 14 Drawing Sheets

(56) References Cited

OTHER PUBLICATIONS

Essaid, H.I., B.A. Bekins, E.M. Godsy, E. Warren, M.J. Baedecker, and I.M. Cozzarelli. 1995. Simulation of aerobic and anaerobic biodegradation processes at a crude oil spill site. Water Resources Research. 31:3309-3327. doi:10.1029/95WR02567.

Jewell, K.P., and J.T. Wilson. 2011. A New Screening Method for Methane in Soil Gas Using Existing Groundwater Monitoring Wells. Ground Water Monitoring and Remediation. 31:82-94. doi: 10.1111/j1745-6592.2011.001345.x.

Tindall, J.A., J.R. Kunkel, and D.E. Anderson. 1999. Unsaturated Zone Hydrology for Scientists and Engineers. Prentice-Hall, Englewood Cliffs, NJ.

Taniguchi, M. 1993. Evaluation of Vertical Groundwater Fluxes and Thermal Properties of Aquifers Based on Transient Temperature-Depth Profiles. Water Resources Research. 29:2021-2026. doi:10.1029/93WR00541.

Tabbagh, A., H. Bendjoudi, and Y. Benderitter. 1999. Determination of recharge in unsaturated soils using temperature monitoring. Water Resources Research. 35:2439-2446. doi:10.1029/1999WR900134.

Sweeney, R.E, and G.T. Ririe. 2014. Temperature as a Tool to Evaluate Aerobic Biodegradation in Hydrocarbon Contaminated Soil. Ground Water Monitoring and Remediation. 34:41-50. doi:10.1111/gwmr.12064.

Suarez, M.P., and H.S. Rifai. 1999. Biodegradation Rates for Fuel Hydrocarbons and Chlorinated Solvents in Groundwater. Bioremediation Journal. 3:337-362. doi:10.1080/10889869991219433.

Sihota, N.J., K.U. Mayer, M.A. Toso, and J.F. Atwater. 2013. Methane emissions and contaminant degradation rates at sites affected by accidental releases of denatured fuelgrade ethanol. Journal of Contaminant Hydrology. 151:1-15.

Sihota, N.J., and K.U. Mayer. 2012. Characterizing Vadose Zone Hydrocarbon Biodegradation Using Carbon Dioxide Effluxes, Isotopes, and Reactive Transport Modeling. Vadose Zone Journal. 11. doi:10.2136/vzj2011.0204.

Siddique, T., R. Gupta, P.M. Fedorak, M.D. MacKinnon, and J.M. Foght. 2008. A first approximation of kinetic model to predict methane generation from an oil sands tailings settling basin. Chemosphere. 72:1573-1580. doi:10.1016/j.chemosphere.2008.04.036.

Revesz, K., T.B. Coplen, M.J. Baedecker, P.D. Glynn, and M. Hult. 1995. Methane production and consumption monitored by stable H and C isotope ratios at a crude oil spill site, Bemidji, Minnesota. Applied Geochemistry. 10:505-516. doi: 10.1016/0883-2927(95)00021-6.

Renno, M.I. 2013. Biogeochemical Characterization of a LNAPL Body in Support of STELA. Master of Science thesis, Colorado State University, Correction: 132 pages.

Rawls, W.J., D.L. Brakensiek, and K.E. Saxton. 1982. Estimation of Soil Water Properties. Transactions of the ASCE. 25:1316-1320.

Ng, G.-H. C., B.A. Bekins, I.M. Cozzarelli, M.J. Baedecker, P.C. Bennett, and R.T. Amos. 2014. A mass balance approach to investigating geochemical controls on secondary water quality impacts at a crude oil spill site near Bemidji, MN. Journal of Contaminant Hydrology. 164:1-15. doi:10.1016/j.jconhyd.2014.04.006.

Zeman, N.R., M.I. Renno, M.R. Olson, L.P. Wilson, T.C. Sale, and S.K. DeLong. 2014. Temperature impacts on anaerobic biotransformation of LNAPL and concurrent shifts in microbial community structure. Biodegradation. 25:569-585. doi:10.1007/s10532-014-9682-5.

McCoy, K. 2012. Resolving Natural Losses of LNAPL Using CO2 Traps. Master of Science thesis, Colorado State University, Correction: 118 pages.

ASTM International. Standard Method D 4373-02: Standard Test Method for Rapid Determination of Carbonate Content of Soil. West Conshohocken, PA: ASTM International, Correction: edition 4373-02, pp. 1-5, 2002.

Lee, C., J. Lee, J. Cheon, and K. Lee. 2001. Attenuation of Petroleum Hydrocarbons in Smear Zones: A Case Study. Journal of Environmental Engineering. 127:639-647. doi:10.1061/(ASCE)0733-9372(2001)124:7(639).

* cited by examiner

ESTABLISHMENT OF CONTAMINANT DEGRADATION RATES IN SOILS USING TEMPERATURE GRADIENTS

CROSS-REFERENCE TO RELATED APPLICATION(S)

This application claims priority to U.S. Provisional Application No. 62/151,564 filed Apr. 23, 2015 and entitled "Establishment Of Biodegradation Rates In Soils Using Vadose Zone Thermal Gradients, Associated Methods, Systems And Devices," U.S. Provisional Application No. 62/158,823 filed May 8, 2015 and entitled "In Situ Measurement Of Soil Fluxes And Related Apparatus, Systems And Methods," and U.S. Provisional Application No. 62/159,445 filed May 11, 2015 and entitled "Apparatus, System And Method For Measuring In Situ Microcosm Degradation Rates," which are hereby incorporated by reference in their entirety under 35 U.S.C. § 119(e).

TECHNICAL FIELD

The disclosed embodiments relate to various methods, systems and devices used to estimate the rate of degradation of contaminants in the ground by measuring temperature gradients in the soil around a reactive zone where heat is produced by contaminant degradation reactions. In certain implementations, the temperature gradients are used to calculate the reactive zone heat flux. Exemplary embodiments quantify the long term, or time-integrated heat flux in the reactive zone, such as over a seasonal period to account for circumstances where the groundwater and surface temperatures vary in a cyclical manner. Exemplary embodiments can also correct for the delay introduced by the rate at which heat produced in the ground is propagated to measurement points. Various implementations are able to reduce or eliminate signal noise, such as the noise caused by changing ambient temperatures and other conditions. Further, a mathematical model is provided to test the validity of the system on two example sites.

BACKGROUND

Contamination of subsurface environments by petroleum and other light non-aqueous phase liquids ("LNAPL") is a widespread problem that raises concerns about contaminant transport and groundwater pollution risks. LNAPL spills often occur due to pipeline breaks or leaking storage tanks near the ground surface. Consequently, large volumes of contaminants often accumulate in the vadose zone and on top of groundwater, generating sources that can pose potential groundwater and/or vadose zone pollution risks for decades. In situ biodegradation by native soil microorganisms (also known as natural source zone depletion, or "NSZD") can have strong effects on the fate of these petroleum hydrocarbon releases under local soil conditions.

The strong dependence of microbial activity and contaminant biodegradation on temperature has been well documented under laboratory conditions. However, the measurement of local (discrete) biodegradation rates in soil has not been widely studied. Accordingly, field data relating degradation rates and soil temperatures is scarce. Recent work has taken advantage of this relationship to use increased groundwater temperatures as a line of evidence for in situ biodegradation. One such study was performed at a former refinery by McCoy, et al, Measurement of Natural Losses of LNAPL Using $CO_2$ Traps. Groundwater. doi: 10.1111/gwat.12240 (2014). Thermal anomalies in the vadose zone at contaminated soils have also been used to estimate aerobic biodegradation rates. However, the coupling of in situ biodegradation rates and soil heat transfer under variable geochemical zones of the vadose zone has not been studied, despite the widespread use of NSZD and enhanced biodegradation at sites across all climates and over a large soil and groundwater temperature ranges.

There is a need in the art for improved systems, methods and devices for establishing biodegradation rates.

BRIEF SUMMARY

Discussed herein are various methods, systems and devices relating to the establishment and use of contaminant degradation rates by way of soil thermal gradients. In certain embodiments, the measurement of a cycle comprises annual data, taken over the course of one or more years. In further embodiments, other durations can be used. In certain embodiments, the measurements are taken between two points in time having the same or substantially similar temperature profiles, such as between spring and fall, or over the course of a single month, depending on the climate and other conditions of the area. Soil temperature measurements are relatively inexpensive and easy to obtain year round, making thermal gradients useful for monitoring NSZD. Methods presented herein are able to estimate the NSZD rate over a season cycle.

The disclosed systems, methods and apparatus address cyclic ambient temperature changes in NSZD. In these circumstances, cyclic ambient temperature changes result in short term heat fluxes not correlated to the reaction heat and can be reversed or otherwise vary cyclically. In these circumstances, failing to account for cyclic variances results in errors in the prior art.

Accordingly, by measuring cumulative heat fluxes across various monitoring locations—on the basis of continuous temperature measurements—the presently disclosed systems, methods and devices are able to counteract or otherwise prevent these errors over time, thereby making the measurement of heat fluxes a quantitative basis to more accurately determine reaction rates. Additionally, the disclosed systems, methods and devices eliminate the need to make measurements at a background location. The disclosed systems, methods and devices include various steps.

In one Example, a system for establishing a rate of contaminant biodegradation in a reactive zone having a soil volume, including at least two temperature sensors configured to record soil data at a perimeter of the reactive zone, a database, the database configured to store the soil data; a central processor in communication with the database; and reaction rate estimation software configured to calculate the rate of contaminant biodegradation from the soil data by establishing temperature gradients at the perimeter of the reactive zone; and time integrated thermal heat flux at the perimeter of the reactive zone over a temporal cycle. Other embodiments of this aspect include corresponding computer systems, apparatus, and computer programs recorded on one or more computer storage devices, each configured to perform the actions of the methods.

Implementations may include one or more of the following features. The system where the reaction rate estimation software is configured to model at least one of the group of including of contaminant degradation reactions methanogenic petroleum degradation, methane oxidation or aerobic petroleum biodegradation. The system where the reaction rate estimation software is configured to establish a biodegradation rate per unit of soil in the soil reactive zone. The system where the reaction rate estimation software is configured to report groundwater heat loss or gains from exothermic soil reactions. The system where the reaction rate estimation software is configured to report the biodegradation rate without performing a background correction. The system where the reaction rate estimation software is configured process at least one of the group including of contaminant biodegradation rates, contaminant distribution, soil properties, ambient temperatures, groundwater temperatures, and combinations thereof. The system where the temporal cycle is selected from a group including about an annual cycle and about a seasonal cycle. The system where the reaction rate estimation software is configured to validate the perimeter of the reactive zone. The system where the reaction rate estimation software is configured to validate the rate of contaminant biodegradation against a biodegradation model. The method where processor is configured process at least one of the group including of contaminant biodegradation rates, contaminant distribution, soil properties, ambient temperatures, groundwater temperatures, and combinations thereof. The method where the exothermic reaction in the soil includes at least one of the group including of methanogenic petroleum biodegradation, methane oxidation or aerobic petroleum biodegradation. The method further including evaluating seasonal dependence of the exothermic reaction due to variable ambient temperatures. The method further including establishing a biodegradation rate per unit of soil in the reactive zone. The method further including reporting groundwater heat loss or gains from the exothermic reaction. The method further including providing a database, the database configured to store the soil data; a central processor in communication with the database; and reaction rate estimation software configured to calculate the rate of contaminant biodegradation from the soil data by establishing the temperature gradients at the perimeter of the reactive zone; and the time integrated thermal heat flux at the perimeter of the reactive zone over the course of a temporal cycle. The method further including providing a processor in communication with a database, where the processor is configured to establish the biodegradation rate of the petroleum from the recorded thermal gradients. The method where the rate of contaminant biodegradation in petroleum contaminated soil includes at least one of the group including of methanogenic petroleum biodegradation, methane oxidation or aerobic petroleum biodegradation. The method further including biodegradation rate against a model. Implementations of the described techniques may include hardware, a method or process, or computer software on a computer-accessible medium.

In one Example, a method of measuring a rate of an exothermic reaction in soil having at least one organic contaminant or contaminant reaction-intermediate, the method including defining a reactive zone perimeter having an outside and an inside including a soil volume containing the at least one organic contaminant or contaminant reaction-intermediate; emplacing at least two temperature measurement devices at the reactive zone perimeter; recording soil data at each of the temperature measurement devices on a database configured to compile soil data; calculating at least one thermal gradient from the soil data from each of the temperature measurement devices on a processor; establishing time integrated heat flux in the reactive zone perimeter on the processor by calculating heat flux over time from the soil data; and determining an exothermic reaction rate of the contaminant or contaminant reaction-intermediate over a temporal cycle on the processor. Other embodiments of this aspect include corresponding computer systems, apparatus, and computer programs recorded on one or more computer storage devices, each configured to perform the actions of the methods.

Implementations may include one or more of the following features. The method where processor is configured process at least one of the group including of contaminant biodegradation rates, contaminant distribution, soil properties, ambient temperatures, groundwater temperatures, and combinations thereof. The method where the exothermic reaction in the soil includes at least one of the group including of methanogenic petroleum biodegradation, methane oxidation or aerobic petroleum biodegradation. The method further including evaluating seasonal dependence of the exothermic reaction due to variable ambient temperatures. The method further including establishing a biodegradation rate per unit of soil in the reactive zone. The method further including reporting groundwater heat loss or gains from the exothermic reaction. The method further including providing a database, the database configured to store the soil data; a central processor in communication with the database; and reaction rate estimation software configured to calculate the rate of contaminant biodegradation from the soil data by establishing the temperature gradients at the perimeter of the reactive zone; and the time integrated thermal heat flux at the perimeter of the reactive zone over the course of a temporal cycle. The method further including providing a processor in communication with a database, where the processor is configured to establish the biodegradation rate of the petroleum from the recorded thermal gradients. The method where the rate of contaminant biodegradation in petroleum contaminated soil includes at least one of the group including of methanogenic petroleum biodegradation, methane oxidation or aerobic petroleum biodegradation. The method further including biodegradation rate against a model. Implementations of the described techniques may include hardware, a method or process, or computer software on a computer-accessible medium.

In one Example, a method of establishing the rate of contaminant biodegradation in petroleum contaminated soil of a defined volume including emplacing at least two temperature sensors within the petroleum contaminated soil; recording thermal gradients from the at least two temperature sensors over about one temporal cycle; and establishing a biodegradation rate for a reactive zone from the recorded thermal gradients. Other embodiments of this aspect include corresponding computer systems, apparatus, and computer programs recorded on one or more computer storage devices, each configured to perform the actions of the methods.

Implementations may include one or more of the following features. The method further including providing a processor in communication with a database, where the processor is configured to establish the biodegradation rate of the petroleum from the recorded thermal gradients. The method where the rate of contaminant biodegradation in petroleum contaminated soil includes at least one of the group including of methanogenic petroleum biodegradation, methane oxidation or aerobic petroleum biodegradation. The method further including biodegradation rate against a model. Implementations of the described techniques may include hardware, a method or process, or computer software on a computer-accessible medium.

One or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Other embodiments include corresponding computer systems, apparatus, and computer programs recorded on one or more computer storage devices, each configured to perform the actions of the methods. In certain embodiments, a system may be provided that includes a processing device and a non-transitory computer-readable medium accessible by the processing device. The processing device may be configured to execute logic embodied in the non-transitory computer-readable medium. One or more computing devices may be adapted to provide desired functionality by accessing software instructions rendered in a computer-readable form.

When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 3A-2 is a continuation of the flow chart of FIG. 3A-1.

DETAILED DESCRIPTION

Figure 1A:
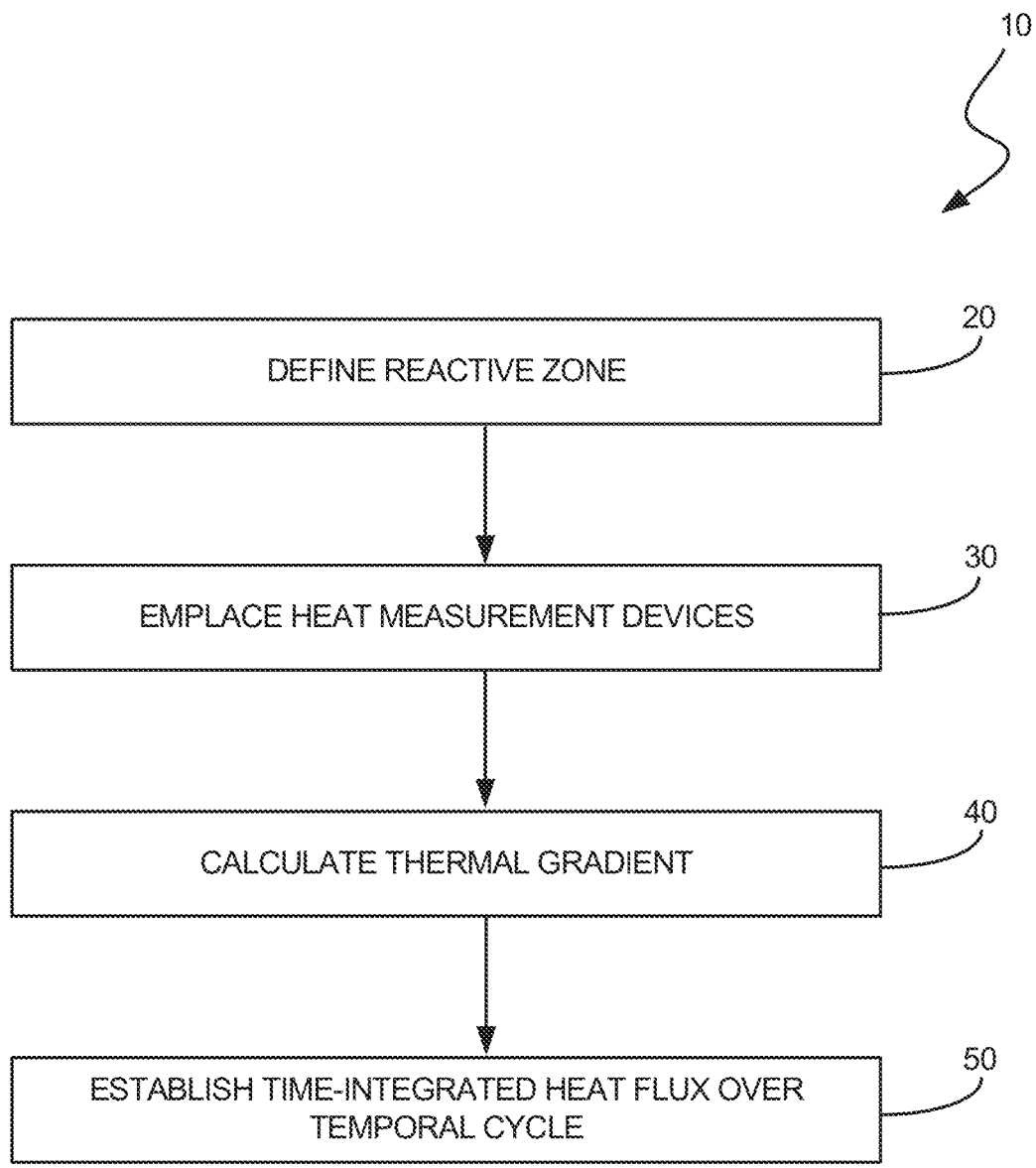
FIG. 1A is a flow chart showing exemplary steps of certain implementations of the system.

Although the present system has been described with reference to preferred embodiments, persons skilled in the art will recognize that changes may be made in form and detail without departing from the spirit and scope of the invention.

As shown in the drawings and description, the various embodiments disclosed or contemplated herein relate to systems, devices and methods of establishing and using contaminant degradation rates by way of soil thermal gradients and associated systems and devices. For brevity, these embodiments may be described in relation to a "temporal heat flux system," 10 though that is not intended to limit the scope of the disclosure in any way.

It is understood that the various embodiments of the temporal heat flux system, methods and devices disclosed herein can be incorporated into or used with any other known contaminant degradation rate systems, methods and devices. For example, the various embodiments disclosed herein may be incorporated into or used with any of the devices, systems and methods disclosed in U.S. Provisional Application No. 62/158,823 filed May 8, 2015 and entitled "In Situ Measurement Of Soil Fluxes And Related Apparatus, Systems And Methods," and U.S. Provisional Application No. 62/159,445 filed May 11, 2015 and entitled "Apparatus, System And Method For Measuring In Situ Microcosm Degradation Rates," all of which are hereby incorporated herein by reference in their entireties.

As shown in FIGS. 1A-8, the disclosed methods, systems and associated devices demonstrate that the use of temperature measurements in the soil can be used to evaluate the rate of exothermic reactions, which generate thermal anomalies in the soil. Due to the facility of obtaining continuous temperature data throughout the soil column, tracking soil temperatures offers a promising technique for establishing contaminant degradation rates.

In the disclosed examples, a simplified model of coupled soil heat transport and petroleum hydrocarbon biodegradation of in the vadose zone was developed to evaluate the effects of local temperatures on contaminant degradation rates. In the disclosed examples, the model was applied at two sites, the Bemidji Crude Oil Research Project ("Bemidji") and at a former refinery in Wyoming ("Wyoming"). The examples include a coupled heat transfer and heat generation model based that includes multiple soil zones that are differentiated by different geochemical conditions, which is discussed in relation to FIG. 2C. The described geochemical conditions result in several reaction mechanisms, each having its own associated reaction heat. Previous studies in this area have been limited to a single type of reaction, such as the aerobic biodegradation of petroleum. This use of a reaction prevalent found only in zones in close proximity to the ground surface and ambient, oxygen-rich air are necessarily more limited in application.

As discussed in the present examples, the data used as model inputs—contaminant degradation rates, contaminant distribution in soil, soil properties, and ambient and groundwater temperatures—were available from previous field studies at these sites and/or published laboratory studies. Implementations include integration of the current vadose zone model with coupled groundwater and heat transport, effectively making the current 1-D model into a full 3-D model. The advantage of this step-wise approach is that heat impacts from methane production from groundwater biodegradation—methanogenic reactions—and subsequent methane off-gassing and oxidation in the vadose zone can be readily accounted for by this current model and the associated examples to reduce the overall noise and/or errors and provide more accurate reaction rate readings.

I. The Temporal Heat Flux System

In exemplary implementations, the temporal heat flux system 10 uses observed temperatures to estimate in situ NSZD reaction rates in a reactive zone 70 of interest. In various implementations described herein, the system 10 can also include a coupled heat generation, or temperature-dependent Monod and heat transfer model, which can be used to validate the results of the estimated reaction rates. Further discussion of the system 10 and model can be found in relation to FIGS. 3A-3C, and the validation of the system 10 with the model can be found in relation to FIGS. 4-8 and in Tables 1 and 2.

Turning to the figures in greater detail, as best shown in FIG. 1A, in exemplary embodiments of the temporal heat flux system 10, several steps are performed. In one step, a reactive zone is defined (box 20). In one step, heat measurement devices are emplaced within a soil region including the reactive zone (box 30). In another step, a processor or module is used to calculate the thermal gradient (box 40). In yet another step, a time-integrated heat flux is established over a temporal cycle (box 50). Further implementations can comprise additional steps.

Returning to FIG. 1A, the presently disclosed heat flux system 10 relates to measuring an exothermic reaction rate in soil of at least one organic contaminant. In certain embodiments, the reaction can be driven by microbes. In further embodiments, the reaction can be driven by chemical oxidants. In various implementations, several optional steps are contemplated by the disclosed systems, methods and devices.

Figure 1B:
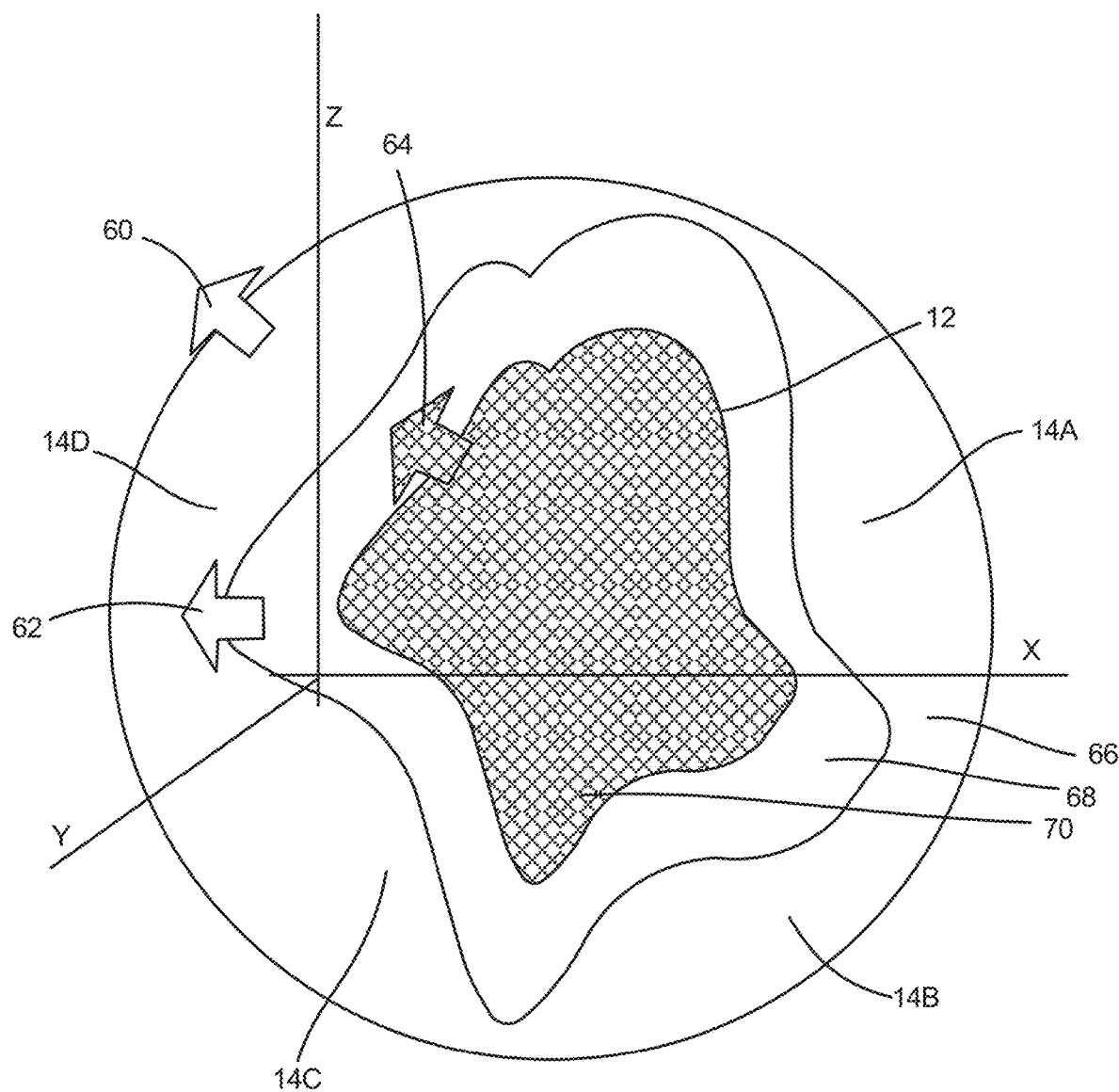
FIG. 1B is a three-dimensional (3-D) schematic of a reactive zone in the soil where reactions occur. Reactions generate a heat flux ($G_{reaction}$) out of the reactive zone.

According to one implementation, to evaluate reaction rates in the reactive zone 70, a first reactive zone perimeter 12 comprising a known volume is defined (shown at box 20 in FIG. 1A). In various embodiments, a first dimension of the reactive zone is further defined by $z_o$ and $z_L$, where $z_o$ is the groundwater level and $z_L$ is the ground surface. An example of one implementation of a reactive zone is shown in FIG. 1B. As used herein, the term "reactive zone" means the area in which exothermic reactions generate heat flux $G_{reaction}$, and can include the vadose zone.

According to one implementation of the system 10, at least two temperature measurement devices 14 emplaced around the first reactive zone perimeter 12 are selected for study. In certain implementations, the temperature measurement devices are thermocouples, wherein each thermocouple has at least two conductors with electrical junctions placed at testing and reference locations with differing temperatures, respectively, to produce a temperature-dependent voltage thereby yielding the temperature. It is understood that each thermocouple pair described herein can be referred to as a single "heat measurement device." In further embodiments, heat flux sensors or transducers can be used though other known temperature measurement devices can be used in alternate embodiments.

In certain implementations, each of the at least two temperature measurement devices is placed at a different altitude. In certain implementations, at least four, at least six, at least eight, at least 10, at least 12, at least 14 or at least 16 temperature measurement devices can be placed in the first reactive zone perimeter 12. In further examples, tens or hundreds of temperature measurement devices 14 can be placed.

Figure 1C:
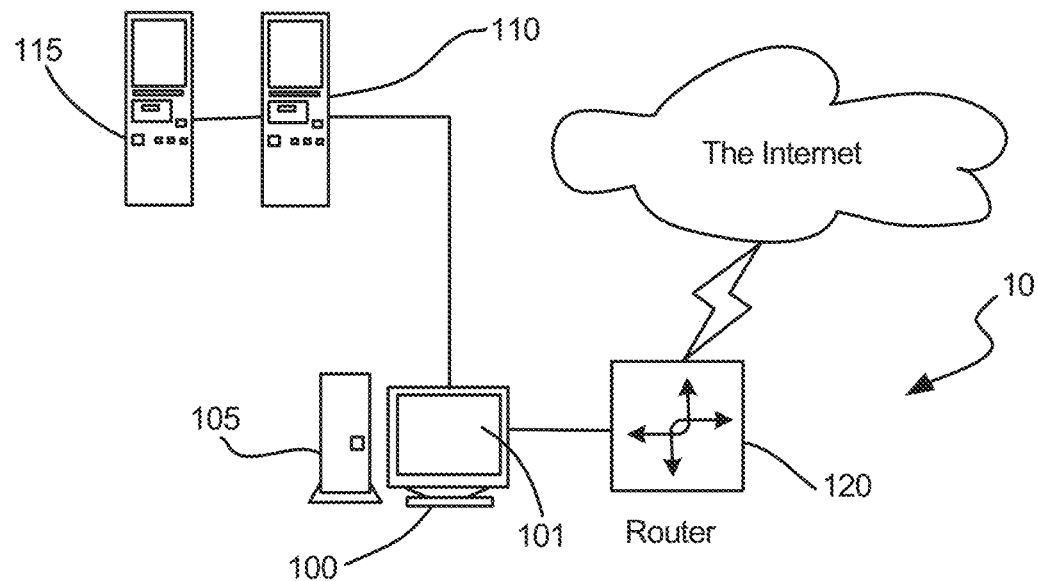
FIG. 1C shows the server and processors running the rate estimation software in communication with the soil database.
Figure 1C:
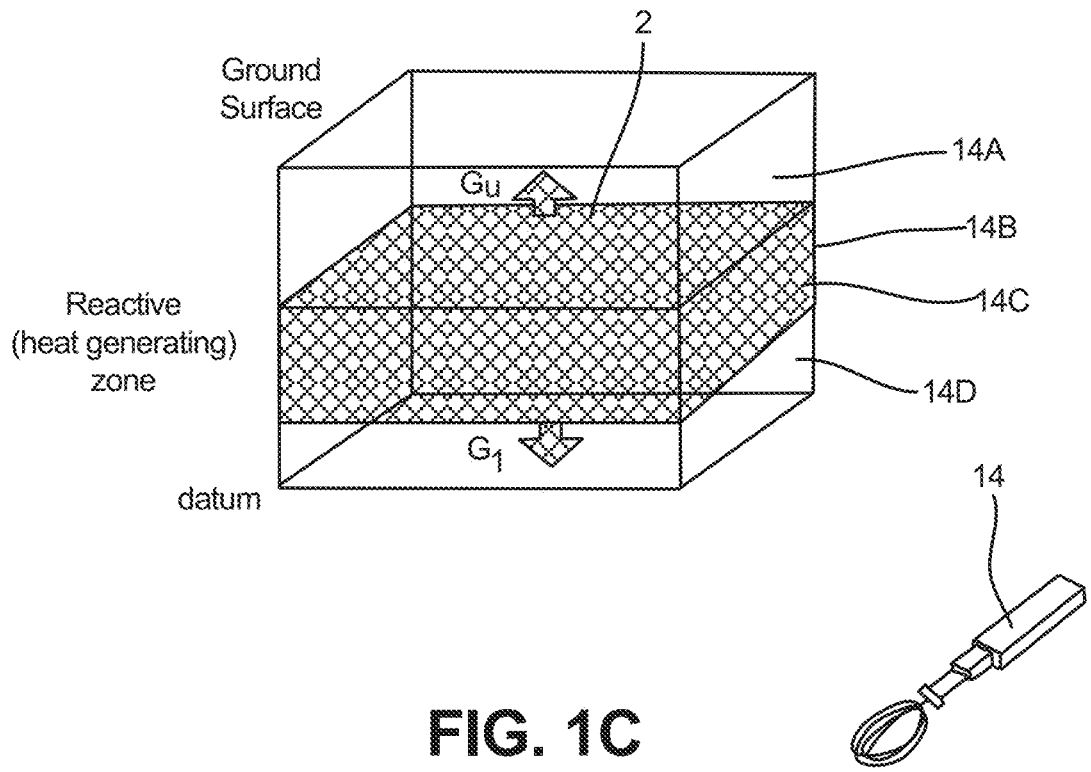

According to one embodiment, as shown in FIG. 1C, the system 10 also has the server or processor or processors 100 running reaction rate estimation software 101. The processor 100 comprises a central processor unit ("CPU") and main memory, an input/output interface for communicating with various databases, files, programs, and networks (such as the Internet), and one or more storage devices. The storage devices may be disk drive devices or CD-ROM devices. The processor 100 may also have a monitor or other screen device and an input device, such as a keyboard, a mouse, or a touch sensitive screen and may be connected to a network and/or server 105.

According to one implementation, the processor 100 is in communication with at least one soil database 110. According to one embodiment, the soil database 110 contains information regarding the time, temperature and depth at each temperature measurement device around the reactive zone, and the accumulation of any other kind of information relating to each temperature measurement device 14A, 14B, 14C, 14D. A parameter database 115 may also be in communication with the processor 100. The parameter database 115 contains information relating to any particular reactive zone, such as contaminant information, reactive zone size information, soil characteristics and the like.

It is understood that the processor 100 can be any computer known to those skilled in the art. In one embodiment, the central processor 100 includes a website hosted in at least one or more computer servers. It is understood that any system disclosed herein may have one or more such server 105 and that each server may comprise a web server, a database server and/or application server, any of which may run on a variety of platforms.

In one implementation, the central processor 100 includes software programs or instructions to process requests and responses. These software programs or instructions perform calculation, compilation, and storage functions, transmit instructions, and generate reports. It is understood that any embodiment of the systems 10 disclosed herein that provide for data collection, storage, tracking, and managing can be controlled using software associated with the system. It is further understood that the software utilized in the various embodiments described herein may be a software application or applications that are commercially sold and normally used by those skilled in the art or it may be a specific application or applications coded in a standard programming language.

It is further understood that the software can be any known software for use with the systems described herein to track, calculate, and manage the various parameters as described herein. For example, as described in further detail herein, various embodiments of the systems described herein could have any one or more of software for tracking time, temperature, corrections, soil characteristics, contaminant information, or software allowing for optimization of any one of these parameters.

The processor 100 allows access to various network resources. In one embodiment, the central processor 100 also has access, via the network 120 or some other communication link, to external data sources that may be used to keep the information in the databases current. In one implementation, a number of site computers may be connected to the server at any given time, and therefore a number of facilities or locations may utilize the system simultaneously.

In the system 10, generally, reactive zone data (such as, for example, time and temperature data, etc.) entered into the system 10 via a client computer or processor 100 is received by the processor 100 or server 105 and stored in any of the appropriate databases of the system.

The databases 110, 115 serve as the inputs to and information storage for the system 10, which processes the information as described below and generates any one or more of notifications, reports, work orders, suggested actions, and/or instructions to a user or to a piece of equipment or a third party system.

Returning to FIGS. 1A-1B, in certain implementations, the system 10 performs an optional measurement step (shown at box 30 in FIG. 1A) on the processor 100, wherein the at least two temperature measurement devices 14A, 14B measure a series of temperature signals $T_{i,t}$, where i is vertical location of the device with respect to the zone and t indicates time. Further discussion of these implementations is found herein in relation to Equations 12A-13.

In various implementations, this measurement step comprises recording and storing the $T_{i,t}$ readings, for example using computer-readable media, such as in data loggers (for example an Omega OM-EL-USB-1). In alternative embodiments, the $T_{i,t}$ readings can be directly transmitted by wireless or wired communications to a recording module located on a server for subsequent.

In certain implementations, a thermal gradient (dT/dz) in the sampled soil is calculated by the system 10 from the temperature signals $T_{i,t}$ received from the at least two temperature measurement devices (shown at box 40 in FIG. 1B). In various implementations, the thermal gradient is calculated over the distance between the at least two temperature measurement devices 14—here i and i+1—given by $\Delta z$. In these implementations, the thermal gradient at a given time t is given by:

$$\left.\frac{\partial T}{\partial z}\right|_t = \frac{T_{i,t} - T_{i+1,t}}{\Delta z} = \frac{T_{i,t} - T_{i+1,t}}{z_{i+1} - z_i} \quad [1]$$

It is understood that the system 10 establishes the time-integrated heat flux in the reactive zone 70, for example over a temporal cycle (shown in FIG. 1B at box 50). In various embodiments, the system 10 utilizes an iterative algorithm so that the heat flux (G) is repeatedly calculated over time $(t_o \rightarrow t_f)$ Accordingly, in these implementations, the heat flux (G) for each of the plurality of times (t) is calculated using the thermal conductivity (K) of the media at the specific time series t:

$$G_t = -K_t \left.\frac{\partial T}{\partial z}\right|_t \quad [2]$$

In certain implementations of the system 10, the exothermic reaction rate or biodegradation rate is calculated over about one temporal cycle (as shown at box 50) by integrating the heat flux calculated over the series of times of the about one temporal cycle. In these implementations, the thermal gradients (dT/dz) are measured as a function of change in heat flux (G) over change in time—the "time-integrated flux"—as follows:

$$\text{Reaction rate} = \frac{\int_{t_o}^{t_f} G_t \, dt}{H_{reaction}} \quad [3]$$

where $H_{reaction}$ is the heat of reaction for contaminant degradation, as described further in relation to Equations 8-9. In certain implementations, this can be an aerobic or anaerobic reaction, as described further below in relation to FIG. 2C and Equations 20-24.

In certain implementations, by defining $t_f$ and to $t_o$ encompass time points when the soil temperature profiles are substantially similar—such as over one temporal cycle of about one seasonal cycle (such spring to fall) or one year—the resulting reaction rate errors introduced from discrete ambient temperature fluctuations are reduced. Further discussion of these implementations of the system 10 can be found in relation to Equations 6-16.

In various implementations, if the soil temperature profiles differ at times tyand $t_o$, the estimate can be corrected based on the known or observed quantity of heat stored in the ground as follows:

$$\text{Reaction rate} = \frac{\int_{t_o}^{t_f} G_t \, dt - \Delta Q_{soil}}{H_{reaction}} \quad [4]$$

In various implementations, $\Delta Q_{soil}$ can be used to define the changes in heat stored in the soil within a time period defined by a final time $t_f$ and an initial time $t_o$. For a perimeter within a 1-D soil column, $\Delta Q_{soil}$ can be calculated using measured depth-dependent soil temperatures and heat capacities, as follows:

$$\Delta Q_{soil} = \int_{z_o}^{z_L} (Cp_f T_f - Cp_o T_o) dz \quad [5]$$

Figures 2A, 2B:
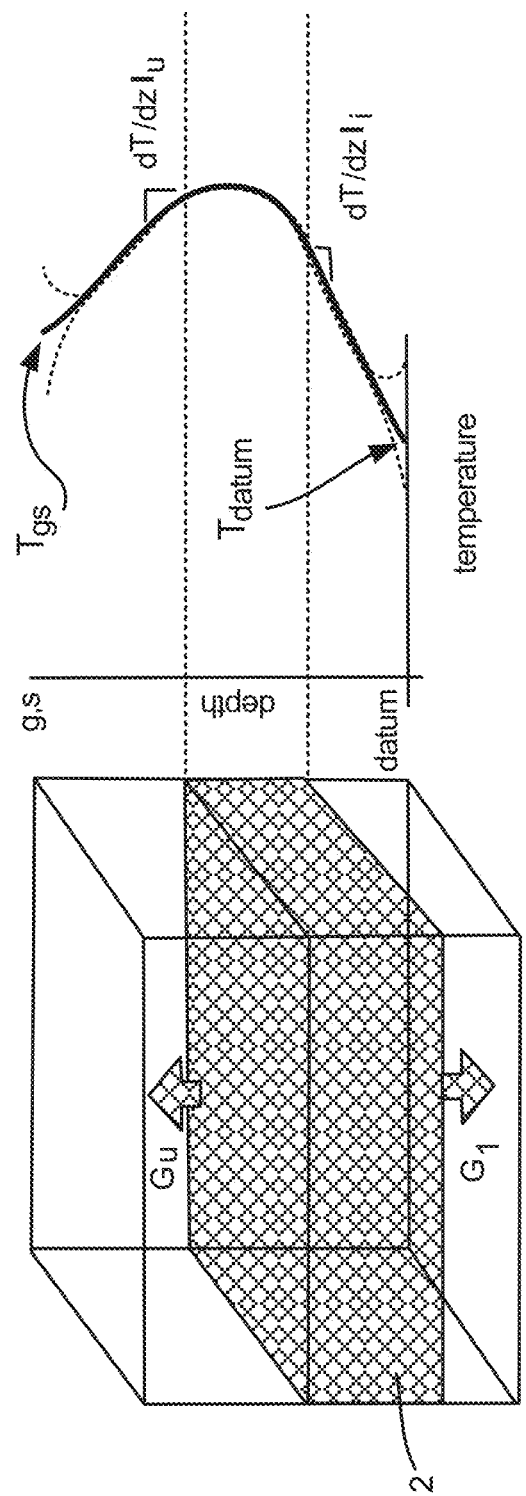
FIG. 2A is one-dimensional (1-D) depiction of the reactive zone of FIG. 1B, showing heat conduction in soil around a soil representative volume element ("RVE") including a reactive zone where exothermic reaction(s) occur.
FIG. 2B shows heat fluxes (G) and thermal gradients (dT/dz) are at two upper and lower boundaries of the reactive zone, using subscripts u and l, respectively.

FIG. 2A shows a 1-D schematic diagram of heat conduction and heat generation in soil. In FIG. 2A, a representative soil volume element is shown, along with the portion of the soil where an exothermic reaction occurs. This 1-D simplification assumes that changes in temperature occur only in the vertical (z) direction. This assumption is justified when the contaminated site has a relatively large ground footprint as compared to the thickness of the contaminated soil.

FIG. 2B shows the soil temperature at different elevations with respect a reference vertical location (datum). The temperature at the ground surface is given by $T_{gs}$ and the temperature at the bottom of the volume element is given by $T_{datum}$. In these examples, $T_{gs}$ can be approximated by ambient temperatures. In circumstances where the datum is at the groundwater level, $T_{datum}$ corresponds to the groundwater temperature. Although the datum location can be anywhere within the reactive zone, the groundwater location is a natural choice, as groundwater temperature is often known. In various implementations, the heat generated within the reactive zone can be conducted—or "dissipated"- to zones above and below the reactive zone and/or datum. It is understood that in certain applications, the reactive zone can extend vertically beyond the vadose zone.

FIGS. 2A-B therefore depict a single "snapshot" in time, in which heat-generating reactions occur at a rate sufficient to raise the soil temperatures higher than in the surrounding soil. In typical prior art approaches, these "snapshot" measurements have been taken as accurate. However, in various implementations, the exothermic reactions are highly dynamic, and can be caused by several temporal changes described herein.

It is understood that in certain circumstances, ambient surface temperatures ($T_{gs}$) vary daily, weekly, monthly, seasonally, annually and the like. In certain circumstances, groundwater temperatures ($T_{datum}$) also vary daily, weekly, monthly, seasonally, annually and the like. Other temperature variations are possible. For example, (as shown in relation to FIGS. 4-8), contaminant degradation rates in soil vary seasonally because of the sensitivity of degradation processes to local soil temperatures. In certain circumstances, reactions that depend on microbes—such as petroleum biodegradation—are particularly affected.

Further, in certain circumstances, changes in soil properties can occur over time, as they depend on soil matrix composition. In these circumstances, events such as precipitation and water infiltration will change the soil composition and its related compositional properties, such as heat capacity, thermal conductivity.

Due to such temporal conditions, transient behaviors can include heat flow reversal near the ground surface, temporal heat accumulation within certain regions of the soil, as well as variable reaction and heat generation rates. In these circumstances, using thermal gradients and time-integrated heat fluxes to estimate degradation rates over longer periods of time, such as seasonally or annually, can address these temporal effects.

Previous studies have accounted for these temporal effects by measuring the temperature profile at both a contaminated location and a non-contaminated location, frequently referred to as a "background correction." However, such background correction assumes that the only difference between impacted and background locations is the contaminant presence, otherwise being identical. In practice, differences in groundwater elevation, lithology and ambient and/or groundwater temperatures between impacted and unimpacted locations can be significant, leading to the introduction of large errors by the correction. For these reasons, the method is not quantitative, and it has been referred to as able to estimate "minimal" degradation rates or relative between locations.

Figures 1, 3A:
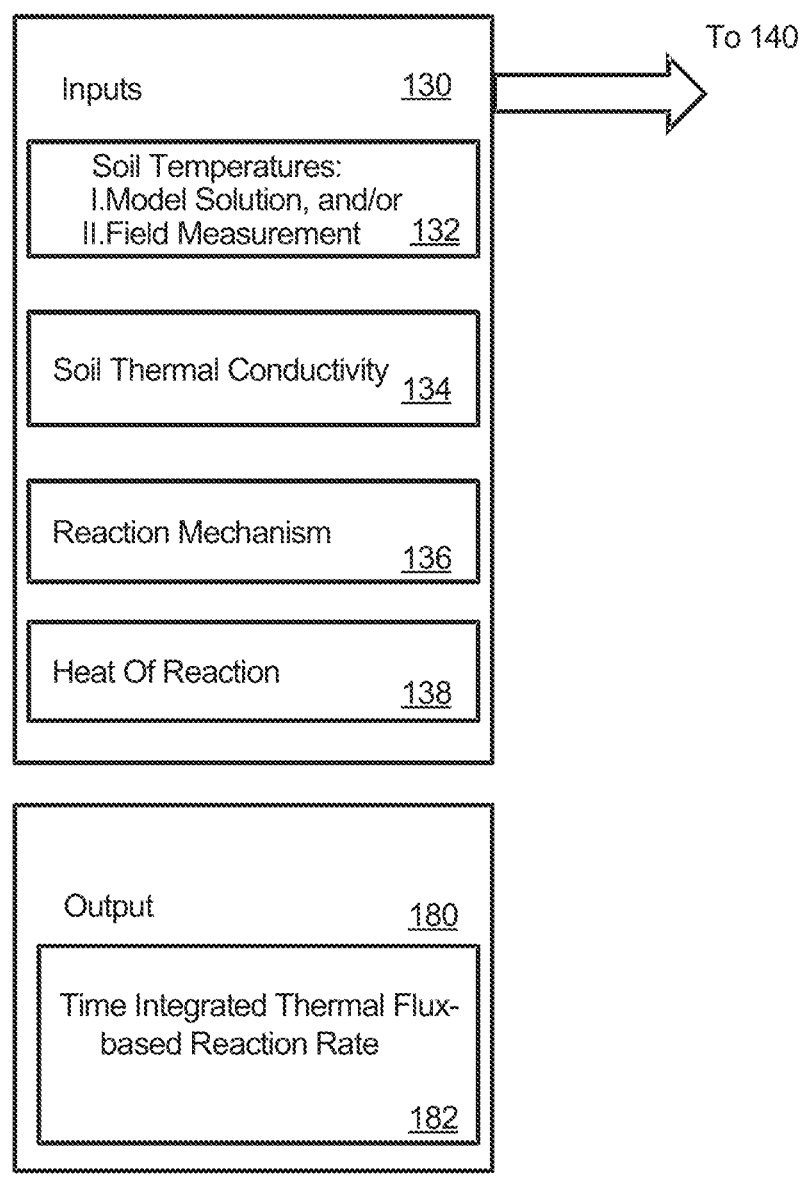
FIG. 3A-1 is a flow chart depicting an overview of the system, according to an exemplary embodiment.
Figures 2, 3A:
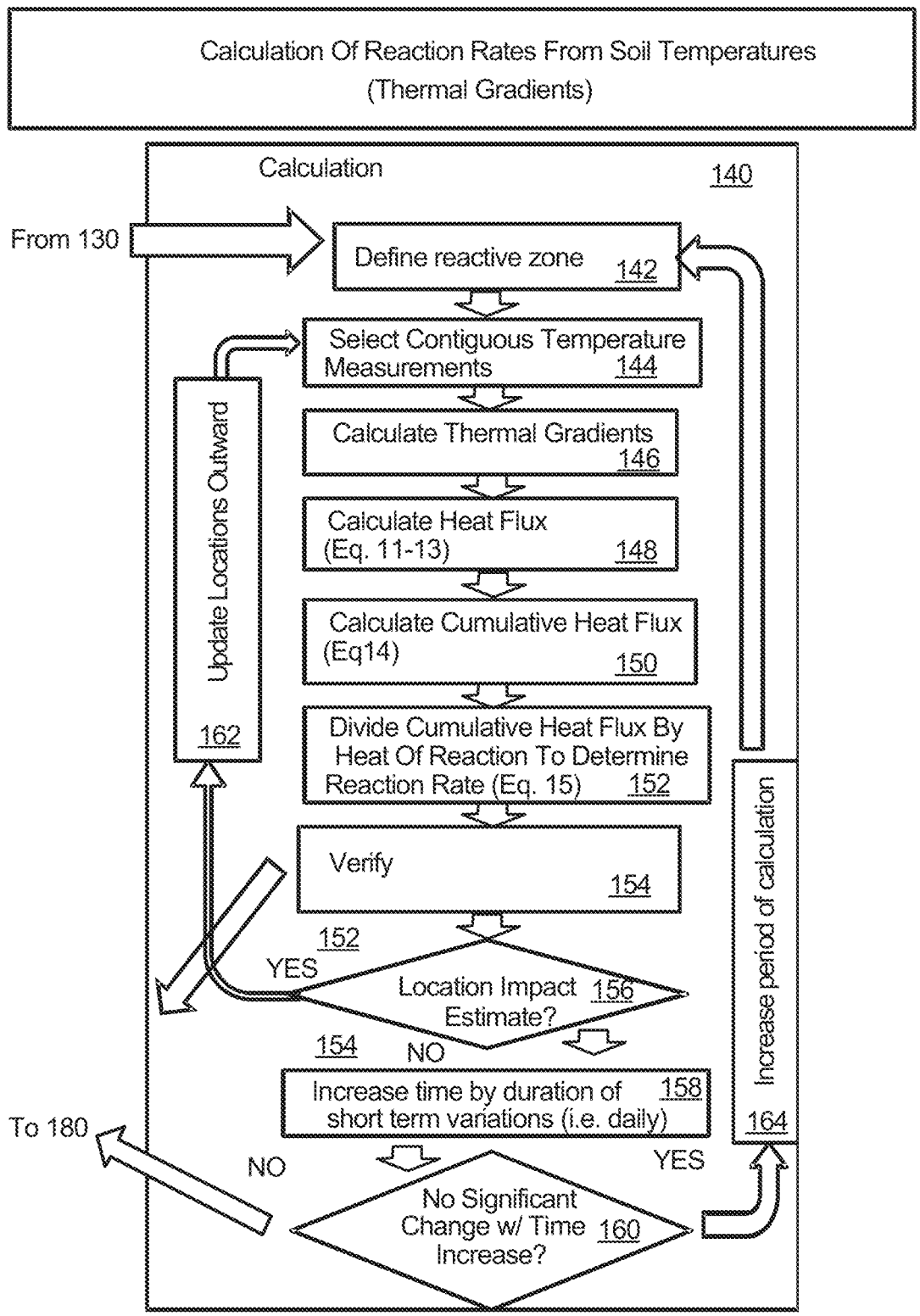

FIGS. 3A-1 and 3A-2 depict a detailed view of various implementations of the system 10, for example running reaction rate estimation software (shown in FIG. 1C at 101).

It is understood that in various implementations of the system 10, several inputs 130 can be used, For example, in various implementations, soil temperatures (box 132) from a model solution (box 132A) and/or field measurements (box 132B) can be inputs. Soil conductivity (box 134), for example as given by equations 6-7 can be used as input. The reaction mechanism (box 136), which can be determined from the local geochemistry (described in relation to FIG. 2C) can be input, as can the heat of reaction (box 138), which can be established by using the reaction mechanism (box 136).

It is further understood that the system 10 is able to use these inputs (box 130) to perform a calculation (box 140). In so doing, the system 10 performs a number of steps in the reactive zone perimeter 12 (discussed above in relation to FIGS. 1A-1C). It is further understood that some or all of these steps may be performed by way of the processor 100 and associated components, as is discussed in relation to FIG. 1C.

In one step, the upper and lower bounding locations of the reactive zone 70 are established (box 142), as is discussed in relation to Eq. 11, below. In another step, at each location, two contiguous temperature measurements are selected (box 144). In a further step, the thermal gradient at each location is calculated (box 146), as is described herein in relation to Eq. 1 and elsewhere. In a further step, the system 10 calculates the heat flux (box 148), as is described in relation to Eqs. 11-13 and elsewhere herein. In a subsequent step, the system 10 calculates the cumulative heat flux over time (box 150), as is described in relation to Eq. 14, below. In a further step (as shown in box 152) the system 10 divides the cumulative heat flux over time (box 150) by the heat of reaction (box 138) to establish the reaction rate, as is described in relation to Eq. 15.

In an optional further step, the system 10 can verify the accuracy of the estimated first reactive zone perimeter 12 (box 154) by querying whether a change in the location of the temperature measurement devices affects the estimate (156). If the change in location significantly affects the estimate, the system 10 can repeat the procedure with a second reactive zone perimeter (box 162), selecting new measurements and repeating the procedure (return to box 144), as is discussed in relation to section D.

In a further step, if the location does not affect the estimate, the time can be increased by the duration of the short term variations (box 158). The system 10 can then query whether a significant change in the estimate was caused by the increase in time (box 160).

If an increase is observed, the calculation period is increased (box 164), and the procedure is repeated. If no, the system can provide a final estimate of the reaction rate as an output (box 180).

It is understood that following the calculation steps (generally at box 140), the system 10 is able to generate outputs (box 180), including the time-integrated thermal flux-based reaction rate over the period of calculation (box 182). A detailed description of the various contemplated steps follows.

A. Heat Flux

Certain embodiments of the system 10 provide for the measurement of heat flux, meaning the measurement of the transport of heat across a defined plane. In various implementations, the heat flux measurement is defined in terms of energy, area and time, and can be given by G.

As shown in FIG. 1B, a reactive zone 70 where contaminants are degraded upon exothermic reactions produces heat. The heat produced by these contaminant degradation reactions is transported through the soil in a diffusion-like process called heat conduction. Heat conduction follows Fourier's law and gives the equation for heat flux:

$$G = -K\nabla T \qquad [6]$$

where G is the heat flux (in units of heat per unit area per time, such as J/m2·s), K is the thermal conductivity of the media—such as soil—in units of Watt/m °C., and ∇T is the temperature gradient in °C./m. The soil thermal conductivity value is the volume weighed average from all different phases in the soil matrix, designated by s, w and a for solid, aqueous and air fractions, respectively:

$$K_{soil} = K_s \phi_s + K_w \phi_w + K_a \phi_a \qquad [7]$$

For a given reaction, the heat of reaction $\Delta H_{reaction}$ is known or can be calculated using standard thermodynamic techniques based on the reaction of interest. For example, consider a reaction where an organic molecule is degraded into inorganic $CO_2$. In various examples, this organic molecule be a contaminant, such as petroleum, or a contaminant byproduct, such as methane —. This process is called mineralization, and is given by:

$$C_n H_m + \left(m + \frac{n}{4}\right) O_2 \rightarrow nCO_2 + \frac{m}{2H_2O} \qquad [8]$$

$$\Delta H_{reaction}\left(\frac{kcal}{mole}\right)$$

In such a mineralization, $\Delta H_{reaction}$ is stoichiometric, meaning that it directly relates to the reaction rate. Under optimum conditions, heat flux leaving the reactive zone—such as the first reactive zone perimeter 12—can be described relative to the reaction rate by the following expression:

$$G_{reaction} = \Delta H_{reaction} Rate_{reaction} \qquad [9]$$

In practice, the exact location of the reactive zone is often not known, so a monitoring zone including the reactive zone can be defined. In these implementations, both reactive 70 and monitoring 68 zones are surrounded by a zone in which ambient temperatures occur ($Vol_{ambient}$) 66. The heat fluxes measured around the reactive ($G_{m,reaction}$) 64, monitoring ($G_{m,monitoring}$) 62, and ambient ($G_{m,ambient}$) 60 volumes are shown in FIG. 1B. In these calculations, the first subscript m, indicates that they are measured based on thermal gradients and the second subscript indicates the location at which the thermal gradient is measured. In various implementations, the reactive zone location and the ambient boundaries are specific aspects of the monitoring location.

FIG. 1B shows a single "snapshot" in time for an idealized condition in which heat-generating reactions occur at a sufficient rate to raise the soil temperatures higher than in the surrounding soil. At steady state, the true heat flux from reaction ($G_{reaction}$) 64 should be equal to the heat flux at the monitoring location ($G_{m,monitoring}$) 62 and also should be equal to the heat fluxes at the reactive zone and also at the interface with ambient ($G_{m,reaction}$ 64 and $G_{m,ambient}$ 60, respectively).

However, the interaction between generation of heat due to reactions and heat transfer in soil is actually highly dynamic due to several processes. Ambient temperatures change daily and seasonally. Heat propagation in soil requires time. In fact, contaminant degradation rates are known to vary seasonally. The interaction of ambient temperatures, heat released from reactions, and heat transfer processes determine local soil temperatures. The sensitivity of reactions to such local temperatures ultimately determines the overall rate of contaminant degradation in soils. However, current approaches to the measurement of reaction rates do not account for such fluctuations.

As a result of these temporal conditions, transient behaviors result in temporal—such as daily and seasonal—heat flow reversal near ground surface, temporal heat accumulation in certain regions of the soil, and variable reaction and heat generation rates. Thus, measured heat fluxes based on temperature gradients at any chosen location (including the monitoring zone, but also at the ambient interface and the reactive zone boundaries) not only includes the heat from reactions, but also the noise generated by cyclic ambient temperature fluctuations around the reactive zone.

Herein, a system 10 utilizing continuous monitoring of temperatures at fixed locations in the soil and calculation of the degradation rates configured to correct for fluctuations over a full seasonal cycle is described. The system enables distinguishing the rate of heat generated within the soil due to contaminant biodegradation reactions from that transferred to/from the surrounding ambient due to ambient temperature variations. The various disclosed embodiments will be illustrated with two examples in which reactions occur in the vadose zone (the zone where soil pores are full of gas). For simplicity, the analysis on these examples will be conducted in one-dimension (1-D).

B. Thermal Gradients

As used herein, the term "thermal gradient" can represent a spatial change in temperatures. In various implementations, thermal gradient is expressed with the units of temperature/length, and can be given by dT/dz.

Figure 2C:
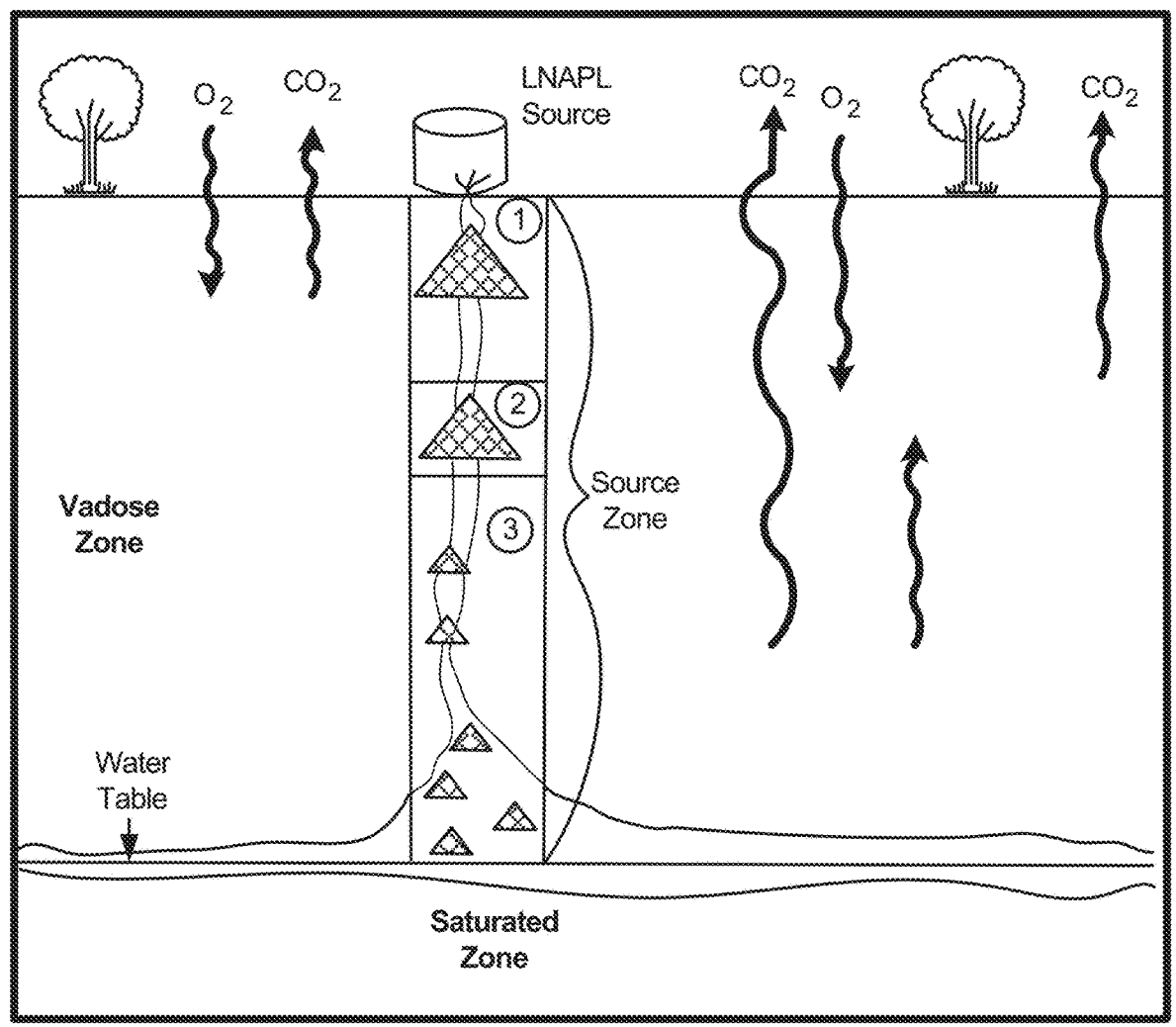
FIG. 2C is a conceptual model of a LNAPL spill site with different geochemical zones. Arrows indicate soil gas transport of reaction products and reactants. Red triangles represent heat released by different biodegradation reactions. Zones identified include: 1) the aerobic biodegradation zone; 2) the methane oxidation zone; and 3) the petroleum anaerobic (methanogenic) biodegradation zone.
Figure 2C:
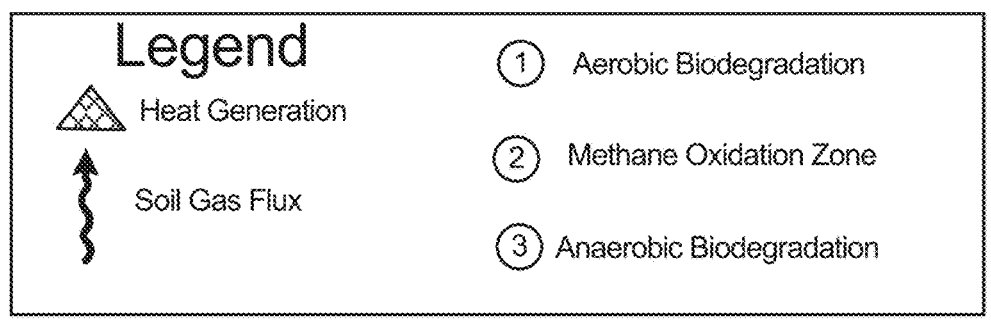

As discussed above, FIG. 2C depicts a conceptual model of heat generation from an LNAPL spill site in several different geochemical zones. In FIG. 2C, the arrows indicate soil-gas transport of reaction products and reactants and the red triangles represent heat released by different biodegradation reactions. The zones identified include the aerobic biodegradation zone, the methane oxidation zone, and the petroleum anaerobic biodegradation zone, which is also known as the methanogenic zone, all of which are discussed in relation to FIG. 2C.

As described in relation to FIGS. 3A-1 and 3A-2, using this 1-D simplification, the relationship between heat fluxes and temperature gradients in Equation 1 (above) can be given by:

$$G_z = -K_{soil} \frac{dT}{dz} \qquad [10]$$

again, where K is the thermal conductivity of the soil, and dT/dz is the thermal gradient.

The total heat flux out of the monitoring zone, defined by the upper and lower reactive zone boundaries ($z_u$ and $z_l$, where $_u$ and $_l$ correspond to the values at the upper and lower boundaries defining the reactive zone, respectively) is as follows:

$$G_{monitoring} = G_u + G_l = -K_u \left|\frac{dT}{dz}\right|_u + K_l \left|\frac{dT}{dz}\right|_l \qquad [11]$$

The sign difference in the formulas for $G_{u,t}$ and $G_{l,t}$ accounts for the geometry of the problem: heat fluxes leaving the reactive zone have a different sign depending on whether they are located above or below such heat generating zone.

In certain implementations of the system 10 (for example as discussed above in relation to box 142 of FIG. 3A-2), the region of interest or reaction zone must be defined. In these implementations, at least two monitoring locations outside of the reactive zone 70 can be defined. Using a 1-D model, these monitoring zones can be defined by $z_l$ and $z_u$. In some cases, $z_l$ can be those at the groundwater level and $z_u$ being ground surface. In these implementations, as the temperature fluctuations at $z_l$ and $z_u$ vary at different scales—for example because ambient temperatures can vary daily—the time interval to record temperatures at each of the selected locations can be adjusted so the temperature variations are captured by the system 10.

In certain implementations of the system 10, a measurement step is performed (box 148 in FIG. 3A-2), wherein at least two temperatures T are measured at neighboring locations around the monitoring points $z_l$ and $z_u$ to determine the thermal gradients dT/dz at each of these locations. In these implementations, by using the thermal gradient dT/dz, the heat flux (G) at a single time t at each of these locations $z_l$ and $z_u$ can be calculated as follows, using the thermal conductivity (K) of the soil at time t:

$$G_{u,t} = -K_{u,t} \frac{\partial T}{\partial z}\bigg|_{u,t} \quad [12a]$$

and $$G_{l,t} = -K_{l,t} \frac{\partial T}{\partial z}\bigg|_{l,t} \quad [12b]$$

for the upper and lower locations, respectively. At each time t, the total heat flux through the monitoring points around the reactive zone 70 is given by:

$$G_{monitoring,t} = G_{u,t} + G_{l,t} \quad [13]$$

In certain circumstances, thermal conductivity (K) can change over time, as is discussed in relation to Eq. 2.

In certain implementations, a correction step can be performed. In certain circumstances, the heat flux estimate requires a thermal conductivity (K) correction. In certain implementations, the correction can be of actual soil moisture levels. In certain implementations, the correction can be based on in situ measurements of this soil property, such as those described in U.S. Provisional Application No. 62/158,823 filed May 8, 2015 and entitled "In Situ Measurement Of Soil Fluxes And Related Apparatus, Systems And Methods," and U.S. Provisional Application No. 62/159,445 filed May 11, 2015 and entitled "Apparatus, System And Method For Measuring In Situ Microcosm Degradation Rates," both of which are incorporated by reference in their entireties.

As shown in FIG. 3A-2 at box 150, in certain embodiments, the average heat flux over a range of time—the time-integrated heat flux ($\overline{G}_{Reaction}$)—can be calculated as the cumulative heat flux divided by the duration of the time interval:

$$\overline{G}_{Reaction} = \frac{\int_{t_o}^{t_f} G_{monitoring,t}\, dt}{t_f - t_o} \quad [14]$$

As shown in FIG. 3A-2 at box 152, in these embodiments, by measuring average heat flux over an extended interval around the reactive zone, it is possible to reduce the effects of short term noise from cyclic fluctuations in ambient or groundwater temperatures. In these embodiments, the long term average reaction rate is therefore given by:

$$\overline{\text{Rate}}_{reaction} = \frac{\overline{G}_{Reaction}}{\Delta H_{Reaction}} \quad [15]$$

In circumstances where the soil temperature profiles and/or the soil saturation—"water content"—differ at the initial and final times ($t_o$ and $t_f$, respectively) the reaction rate estimate can be corrected based on differences in heat stored in the monitoring portion of the ground as follows:

$$\overline{\text{Rate}}_{reaction} = \frac{\int_{t_o}^{t_f} G_{monitoring,t}\, dt - \Delta Q_{soil}}{\Delta H_{Reaction}(t_f - t_o)} \quad [16]$$

where $\Delta Q_{soil}$ is the change in heat stored in the soil within a time period defined by a final time $t_f$ and an initial time $t_o$. For a perimeter within a 1-D soil column, $\Delta Q_{soil}$ is calculated using soil saturation depth-dependent soil temperatures and heat capacities, thereby yielding Equation 5, discussed further above:

$$\Delta Q_{soil} = \int_{z_l}^{z_u} (\rho_f Cp_f T_f - \rho_o Cp_o T_o)\, dz \quad [5]$$

C. Cumulative Heat Flux Measurements

In various embodiments of the system 10, heat flux data can be compiled cumulatively. In these implementations, the system 10 can tabulate cumulative heat fluxes to establish cumulative total flux $G_{total}$. In these implementations, when the addition of a discrete short term heat flux measurement G to the cumulative total $G_{total}$ does not result in a statistically significant change (such as less than about 1%), the cumulative heat flux $G_{total}$ can be used as an adequate estimate of the time-integrated heat flux.

D. Defining The Reactive Zone

In various implementations of the system 10, the contours of the reactive zone 70 can be further defined. "Missing" the reactive zone 70, such as by locating the temperature measurement devices 14 within the reactive zone 70, will introduce errors into the observed reaction rates. In these implementations, additional reactive zone perimeters can be used to more accurately define the reactive zone 70 and more accurately establish the reaction rates.

In certain applications, the temperature measurement devices 14 are emplaced at imprecise locations around the first reactive zone perimeter 12 (preferably at the upper and lower boundaries in a 1-D model). For example, in certain implementations, at least four temperature measurement devices 14 are disposed at various heights in a well.

Flux measurements recorded from such imprecisely located temperature measurement devices 14 can therefore be flawed. In certain implementations of the system 10, several temperature measurement devices 14 can be deployed around the reactive zone 70 and can be used to improve/validate the proper location for the estimated reaction rate. In these implementations, several steps may be performed.

In one step, two temperature measurement devices 14 are disposed around the reactive zone 70 are selected or emplaced and used to estimate the first reactive zone perimeter 12 heat flux (here, $G_1$), as described elsewhere herein.

In another step, the temperature measurement devices 14 can be relocated outward from center of the reactive zone 70, or a new set of more distant temperature measurement devices 14 can be selected (in either case, defining the second reactive zone perimeter 22). Following this step, the second reactive zone perimeter 22 is used to calculate a second perimeter heat flux $G_2$.

In these implementations, if the estimate from the second reactive zone perimeter 22 does not differ significantly from first reactive zone perimeter 12, then the first reactive zone perimeter 12 can be validated. If a significant difference is observed, the above steps can be repeated to establish a third reactive zone perimeter (not shown) and so on, in an iterative manner.

Further, in certain implementations, the process of defining the reactive zone can be combined with a cumulative calculation of heat flux to establish when short term noise is no longer significantly impacting the cumulative calculation of heat flux $G_{total}$ described above.

In various applications, precisely defining the reactive zone 70 is useful to the heat flux estimate, as would be appreciated by a skilled artisan, but can also be useful by itself, as it would provide insight into where the exothermic reactions are occurring.

II. Model for Coupled Heat Transfer and Heat Generation from Petroleum Biodegradation in Soil To validate and calibrate the accuracy of the presently described system 10, a model 200 from previous work was developed.

Figure 3B:
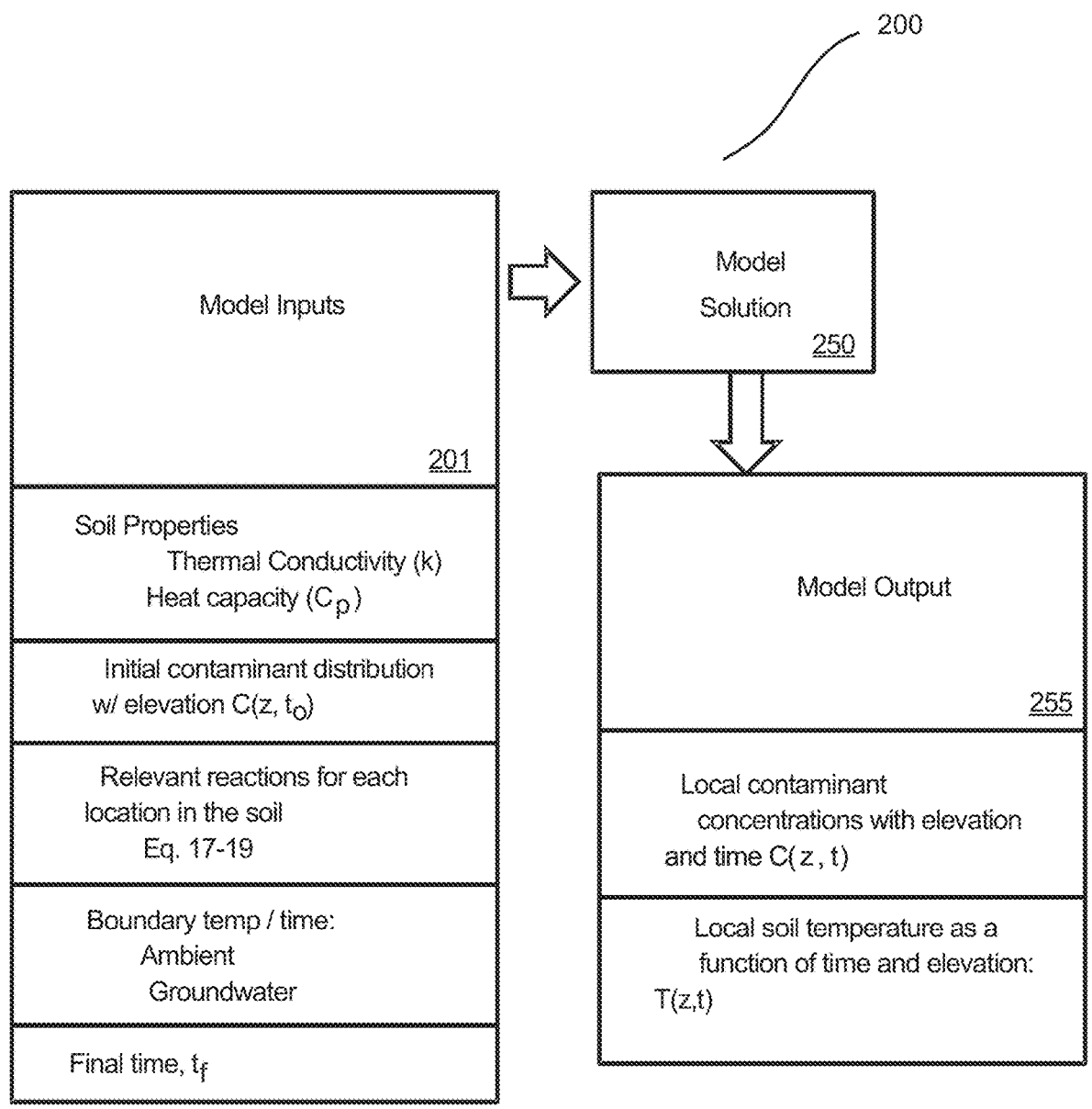
FIG. 3B is a flow chart depicting an overview of the validation model, according to an exemplary embodiment.

It is understood that in various implementations, the model 200 performs several steps, as is shown generally in FIG. 3B. In one implementation, the system compiles various model inputs (box 201), performs a model solution (box 250) and generates a model output (box 255). Further discussion of each of these steps follows.

Figure 3C:
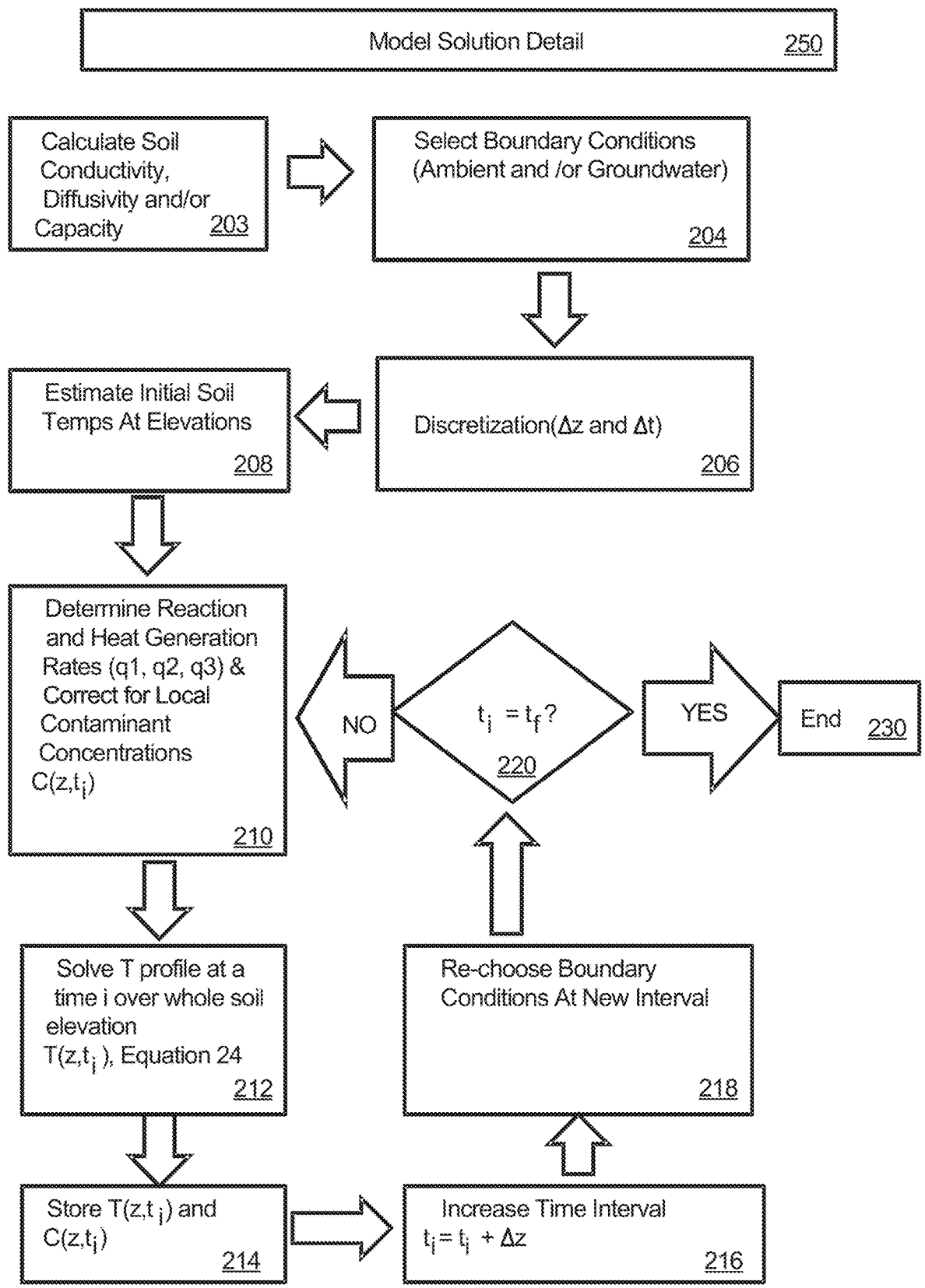
FIG. 3C is a flow chart depicting an exemplary embodiment of the model solution.

As shown in FIG. 3C, in exemplary implementations, the model comprises a variety of steps. As shown in box 203, the soil thermal conductivity value, diffusivity and/or heat capacity of the soil matrix can be established using Eqs. 7, 25 and 26. As shown in box 204, the initial boundary conditions at an initial time ($t_i=t_o$) can be selected, representing the ambient and groundwater temperatures. As shown in box 206, a discretization step can be performed, where the total elevation ($\Delta z$) and time and ($\Delta t$) are distributed into multiple intervals.

Continuing with FIG. 3C, in box 208 the initial ($t_i=t_o$) soil temperatures are estimated at other soil elevations $T(z,t_o)$. In box 210, Eq. 20 can be used at each time ($t_i$) and elevation (z) to determine heat generation rates using q1, q2, q3 from Eqns. 21B, 22B, 23B, and the local contaminant concentrations $C(z,t_i)$ can be corrected based on given reaction rates. In box 212, the T profile can be solved at each time (i) over the entire soil elevation $T(z,t_i)$ using Eq. 24. In box 214, the time and concentration calculations for ($t_i$) ($T(z,t_i)$ and $C(z,t_i)$) can be stored in the database, as discussed above. In box 216, the time interval is increased, $t_i=t_i+\Delta z$, and in box 218, new boundary conditions can be selected. In box 220, a comparison is made between the assessed time and final time ($t_i=t_f$); if equal, the process is ended (box 230), if not, the process resumes at box 210.

As discussed herein, the presently disclosed heat flux system 10 was applied and model-validated at two sites, the Bemidji oil spill site in Minnesota (the Bemidji Crude Oil Research Project, which is managed by the USGS) and at a former refinery in Wyoming. The data used as inputs—biodegradation rates, contaminant distribution, soil properties, and ambient and groundwater temperature—were available from previous field studies at these sites and or published laboratory studies. Implementations include integration of the mathematical model coupled with a groundwater and heat transport model. The advantage of this step-wise approach is that heat impacts from methane production from methanogenic groundwater biodegradation reactions and subsequent methane off-gassing and oxidation in the vadose zone can be readily accounted for by this model.

A. Exothermic Reactions

Contaminant biodegradation reactions are exothermic, meaning that they produce energy. This energy is used by microbes to grow and to fuel their metabolism. Once a microbial population is established on a contaminated site undergoing natural source depletion (NSZD) the mass o biomass stabilizes. Although this condition will likely change over large periods of time (years or months, as source depletion might affect long term contaminant composition, or as local soil temperatures change seasonally), changes over the short term (i.e., days or weeks) can be assumed negligible. This condition is known as a pseudo-steady state. Under such pseudo-steady state, microbial growth rates are relatively small, and most of the energy results in heat released to the soil. Such resulting heat is proportional to the NSZD rates, as the heat of these reactions is stoichiometrically related to the extent of reactions by well-understood thermodynamic relationships.

In practice, the actual reactions that occur at different soil locations are determined by the local geochemistry. A conceptual site model for petroleum hydrocarbons and local geochemical conditions has been described earlier (as shown on FIG. 2C). These geochemical gradients are defined by available electron acceptors. An aerobic and an anaerobic zone are clearly differentiable depending on the presence or absence of oxygen. The interface between these two zones is known as the aerobic/anaerobic ("A/A") interface.

Assuming that the LNPAL contaminant is represented by an example generic hydrocarbon (i.e., octane, $C_8H_{18}$), the reactions relevant to this conceptual model are:

$$C_8H_{18} + 12.5O_2 \rightarrow 8CO_2 + 9H_2O \quad \Delta H_{aerobic} = 1{,}224\frac{kcal}{mole} \quad [17]$$

$$C_8H_{18} + 3.5H_2O \rightarrow 6.25CH_4 + 1.75CO_2 \quad \Delta H_{methanogenesis} = 24\frac{kcal}{g\ HC} \quad [18]$$

$$6.25CH_4 + 12.5O_2 \rightarrow 6.25CO_2 + 12.5H_2O \quad \Delta H_{CH4ox} = 1{,}200\frac{kcal}{g\ HC} \quad [19]$$

The $\Delta H$ of Eqs. 17-19 were calculated from standard heats of formation, as is known to the skilled artisan. In Eq. 19, the methane oxidation is based on an assumed 6.25 moles of methane, as that is the amount of methane produced per mole of the example hydrocarbon $C_8H_{18}$. Thus, the heat of reactions is shown on a comparable basis per one mole of degraded hydrocarbon. Although reactions using other terminal electron acceptors—including TEAs, such as sulfate, iron, nitrate and the like are possible these are in limited supply at contaminant source zones. After an initial spill, TEAs are typically depleted, thereby leaving methanogenesis as the dominant anaerobic process at source zones.

Accordingly, in this example, the methane resulting from Eq. 18 diffuses upwards and reacts with ambient oxygen to generate $CO_2$, per the reaction of Eq. 19. As methane is readily biodegraded by aerobic microbial soil populations in the presence of oxygen, methane oxidation often occurs rapidly in a narrow soil band.

In this example, the heat from Equation 19 is about 98% of the heat from Eq. 17. Conversely, the heat produced under anaerobic conditions (Eq. 18) is nearly two orders of magnitude smaller than that from aerobic biodegradation (Eq. 17). These very different heat values of these reactions highlights the need to understand the specific kinds of reactions occurring at different soil levels before estimating reaction rates.

The conceptual site model described above implies that some of these reactions might be mutually exclusive—such as aerobic vs. anaerobic—or can be co-located—such as methane oxidation and aerobic degradation. Heat generated from degradation of natural soil organic matter was not considered in this study since it is about one order of magnitude smaller than the heat from petroleum degradation.

B. Model Components

1. Exothermic Reaction Kinetic Component

Under the Monod equation, biodegradation reaction kinetics depend on the concentration of the microbial substrate or contaminant. When the microbial biomass achieves steady-state, the Monod kinetics expression for reaction rate is given by:

$$-\frac{dC}{dt} = \frac{k_{max}C}{C+C_m} = \frac{k_0 C}{C+C_m} \quad [20]$$

where $$\frac{dC}{dt}$$

is the change in contaminant concentration over time (reaction rate), $C_m$ is the half-saturation constant, and $k_{max}$ is the maximum biodegradation rate, which is equal to the zero-order biodegradation rate ($k_0$). The Monod constants ($k_{max}$ and $C_m$) are reaction specific, meaning they differ for aerobic or anaerobic conditions and/or based on different substrates. The present kinetic model predicts a constant biodegradation rate at high LNAPL concentrations—where $C \gg C_m$—and first-order rates at low LNAPL concentrations—where $C \ll C_m$.

2. Biodegradation-Related Heat Generation

FIG. 2C is a conceptual model of a LNAPL spill site with different geochemical zones: 1) the aerobic biodegradation zone; 2) the methane oxidation zone; and 3) the anaerobic biodegradation zone. In a 1-D model, the depths of these zones are given by the ground surface and the aerobic/anaerobic interface (for the aerobic degradation zone), and by the aerobic/anaerobic interface and a shallow location where methane is no longer available (for the methane oxidation zone), and 3) the anaerobic/aerobic interface and a lower, deeper datum. The heat generation rates of each of the biodegradation reactions included in the system 10 are discussed below: methanogenic LNAPL degradation, methane oxidation, and aerobic LNAPL degradation.

Methanogenesis.

Methanogenesis occurs in the lower anaerobic biodegradation zone shown in FIG. 2C, and the reaction for a generic alkane ($C_n H_{2n+2}$) is given by:

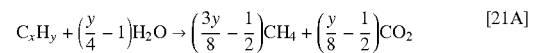

$$C_x H_y + \left(\frac{y}{4} - 1\right)H_2O \rightarrow \left(\frac{3y}{8} - \frac{1}{2}\right)CH_4 + \left(\frac{y}{8} - \frac{1}{2}\right)CO_2 \quad [21A]$$

In various implementations, the system 10 accounts for the quantity of heat generated by methanogenesis ($q_1$) as follows:

$$q_1 = \Delta H_{methanogenesis} * \frac{dC}{dt} \quad [21B]$$

where dC/dt is the reaction rate for methanogenesis.

Methane Oxidation.

In FIG. 2C, methane oxidation occurs in the middle methane oxidation zone, and is given by:

$$CH_4 + 2O_2 \rightarrow CO_2 + 2H_2O \quad [22A]$$

In various implementations, the heat produced by methane oxidation ($q_2$) in this finite layer is calculated through the integrated LNAPL concentration loss in the anaerobic zone as follows:

$$q_2 = \frac{\Delta H_{CH4ox}}{w} = \int_{z_{GW}}^{z_b} \frac{dC}{dt} dz \quad [22B]$$

where $\Delta H_{CH4ox}$ is the heat of reaction for methane, $z_b$ is the bottom of the methane oxidation zone (i.e. the depth at which the anaerobic zone begins), $z_{GW}$ is depth to groundwater, and w is the width of the methane oxidation zone.

Equations 22A and 22B are sequential, and imply that heat released from methane oxidation occurs at a different location than petroleum degradation. Accordingly, methane is produced in the anaerobic zone (given by Equation 21A) and it is assumed to transport upward relatively rapidly to the methane oxidation zone, where it degrades in a fast reaction upon contact with atmospheric oxygen diffusing into the vadose zone and is therefore not rate limiting.

The location of this zone was assumed constant, although field measurements could be used to correct its seasonal dependence, as the location and thickness of this zone might depend on the magnitude of the counter-diffusive fluxes of methane and oxygen, both of which might vary seasonally.

Aerobic Biodegradation.

In certain circumstances, aerobic degradation of LNAPL occurs in cases where LNAPL is present in the upper soil layers that are close to the oxygen-rich ambient air. Typically, however, upper soil layers typically do not contain large quantities of LNAPL, as has been demonstrated in the former refinery site discussed below. However, other sites do present aerobic zone LNAPL, such as in the Bemidji site discussed below. Accordingly, in certain implementations the system 10 accounts for the aerobic biodegradation of LNAPL. The basic chemical equation for aerobic petroleum hydrocarbon oxidation is:

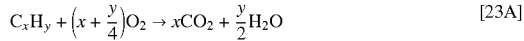
[23A]

As with the methanogenic petroleum degradation, the Monod-based reaction rates and the corresponding thermodynamic heat generation from aerobic oxidation directly depend on the location specific LNAPL concentrations. In various implementations, aerobic oxidation is accounted for from ground surface to the depth of the anaerobic zone (given by $z_b$). In these implementations, the equation for aerobic biodegradation ($q3$) is given by:

$$q_3 = \Delta H_{aerobic} * \frac{dC}{dt} \quad [23B]$$

where $\Delta H_{aerobic}$ is the heat of reaction for aerobic oxidation. Aerobic oxidation and methanogenesis were assumed to take place at the same rate, meaning having equal values for the Monod constants, which is consistent with previous results.

3. Coupled Heat Propagation And Reaction Component

In various implementations, the second law of heat conduction can determine the propagation of internally generated heat due to methanogenesis ($q_1$) in the soil:

$$\frac{\partial T}{\partial t} = \alpha \frac{\partial^2 T}{\partial z^2} + \frac{q_i}{\rho c_p} \quad [24]$$

where $$\frac{\partial^2 T}{\partial z^2}$$

is the second derivative of the change in temperature with respect to depth, and $q_i$ represents the heat generation rate per unit volume due to specific biodegradation reactions and $\alpha$ is the thermal diffusivity of the media.

Accordingly, in some implementations the thermal diffusivity of soils is calculated as follows:

$$\alpha = \frac{k}{\rho C_p} \quad [25]$$

The bulk properties of both thermal conductivity and heat capacity are composition-weighed properties. In various implementations, the product of density and heat capacity is estimated as follows:

$$\rho C_p = (\rho C_p)_s \phi_s + (\rho C_p)_w \phi_w + (\rho C_p)_a \phi_a \quad [26]$$

Equation 26 allows the estimation of the heat capacity of the soil matrix ($C_p$) as a composition-weighted average, where $\rho$ is density, and $\phi$ is volume fraction, and the subscripts s, w, and a represent the soil, water and air components, respectively.

In exemplary embodiments of the system, a temporal heat flux system 10 is provided. In various embodiments of a system, a model is used to estimate reaction rates. The model consists of several components described above, including those in relation to Equations 20-24.

4. Model Solution And Validation

Atmospheric and groundwater temperatures vary seasonally and generate heat fluxes into and out of the soil. These heat fluxes interact with heat generated from contaminant biodegradation. In one example, groundwater and ambient temperatures were used as model input boundary conditions from actual field measured data. Accordingly, these conditions are assumed to be imposed on the system 10, rather than being calculated by the model. The temperature dependence of biodegradation rates (Eq. 20) was based on results from laboratory microcosm studies. Model calibration was performed using available site specific measured field biodegradation rates from previous reports.

In this example, the model is a transient, one dimensional (1-D) vertical, or depth model. In this example, the use of rectangular coordinates is justified by the much larger scale of the horizontal LNAPL as opposed to the height of the vadose zone. In further implementations, other coordinate structures can be used, as would be apparent to the skilled artisan.

The present model was solved using a numerical finite difference approximation of the partial derivatives (coded in Anaconda Python 2.7, Continuum Analytics). Partial derivatives of temperature with respect to time and space were solved implicitly, or "backward" in time. The discretization of the second partial derivative of temperature in space was obtained using the implicit and explicit (forward in time) first derivative approximations. The Neumann stability criterion, given by:

$$\left(\Delta t \leq [(\Delta x)]^{\frac{2}{2\alpha}}\right) \quad [27]$$

was used to determine grid-spacing ($\Delta t$) along the x-axis of the finite difference approximation, where $\Delta t$ is the grid spacing along the time domain and $\Delta x$ is the grid spacing along the depth domain.

Heat production for methanogenesis ($q_1$) and aerobic oxidation ($q_3$) (Equations A and C) depend on contaminant concentrations that vary with location in the soil column, while heat from methane oxidation ($q_2$, Equation B), represents uniform heat generation rate within the methane oxidation zone. The code to solve Eqs. 20-24 was validated by setting $q_1=q_3=0$, extending the methane oxidation zone to encompass the entire vadose zone, and adjusting boundary conditions to a constant temperature (7).

Under these settings, the problem becomes identical to a finite slab with uniform internal heat generation. The analytical solution to this problem was used to validate the temperature profiles predicted by the numerical model. Additionally, based on Example 1 (discussed below) the pseudo-steady state heat flux calculated from thermal gradients under constant boundary conditions (surface and groundwater temperature) matched the Monod kinetics-based model predicted contaminant loss.)

Example 1: Former Refinery Site

The model was applied to a former refinery site to validate the method (invention). The site is located in a dry, high desert environment in the western US, and has distinct cold and warm weather seasons. The site was used for petroleum refining and production of asphalt and coke. Measured LNAPL concentrations vs. depth from soil cores in transect C3 were used as model input. The zone for methane oxidation (1.1 m to 2.3 m below ground surface) was determined from field measured subsurface $CH_4$ and $O_2$ gas concentrations, and is consistent with identification of methane oxidizing microbes based on DNA analysis. The soil at this site is mostly fine to medium sand and was assumed to be at residual water saturation (3%) due to the arid climate of the region. Based on this moisture level, the thermal conductivity for this soil type (k) is known to be 0.8 J/m·K·s, the residual water content, and estimated porosity of 44% results in a thermal diffusivity $\alpha=6.06*10^{-7}$ m$^2$/s. The calculated a value is consistent with reported values for unsaturated sandy soil. Daily median temperatures for the 2011 calendar year from NOAA station GHCND: USC00481569—about 2 miles West from the site—were used as the surface temperature boundary condition. The groundwater temperature boundary condition for the same period was available from measured groundwater temperatures in nearby well A2).

The majority of the former refinery contaminants were observed to be in the $C_6$ to $C_{28}$ range. Octane ($C_8H_{18}$) was considered a representative formula of the contaminant. Three measurements of petroleum biodegradation rates are available from literature at the same location at this site, conducted by measuring $CO_2$ fluxes at ground level.

I. Kinetic Data

Monod kinetic parameters were reported from previous work used to predict methane generation from oil sands at 22° C. Based on reported values for first-order reaction rates for n-octane at 22° C., $k_o$ and $C_m$ were calculated to be 1.54 kg/m$^3$ yr and 0.476 kg/m$^3$ respectively. The dependence of biodegradation rates on temperature was obtained from previous laboratory microcosm studies which quantified biogas production rates in a temperature range of 4–40° C. Temperature dependent zero-order biodegradation rates were calculated from biogas production rates and used as model inputs. The data from this microcosm study at 22° C. was within 1% of the previously observed $k_o$ value from Siddique et al., thereby showing remarkable consistency between laboratory and field data from both research groups. The previously reported biogas production by Zeman et al. was null at 9° C., although the same report showed measurable contaminant biodegradation at the same temperature. As previous research documented degradation in the range of 5-10° C. temperature range, it was determined that the 9° C. data point was inconsistent, and it was therefore was omitted, resulting in interpolated estimates between 4° C. and 22° C. from measurements at the end points of this range.

II. Model Calibration

In order to calibrate the model for the former refinery zero-order rates from soil microcosm, the experiments were adjusted so that model outputs of LNAPL concentration loss matched field estimates of LNAPL loss from $CO_2$ fluxes. The data from encompassed three sampling events at different times of the year, allowing a three-point calibration for the former refinery site. Expressed as a multiplier of the lab microcosm data, field zero-order rates fitted in this manner were 1.3 times higher that those for the former refinery. These scaling factors imply that the field rates are within one order of magnitude of those from microcosm studies. Model solutions developed in this manner offer a way of allocating the heat production rate within the soil due to biodegradation reactions observed at field sties consistently with kinetic data available from other laboratory studies.

Equation 6 provides the basis to estimate soil heat flux, G in J/m$^2$ s, from temperature gradients given by dT/dz. In various implementations of the system 10, G can be converted to estimates of LNAPL loss (kg/m$^2$ yr) using the known heat of biodegradation for the specific compound being degraded (for example by using Eqs. 12-15, above). Accordingly, the total heat flux (G) in a one-dimensional system (1-D) encompasses heat flow across two boundaries, such as the top and bottom of a soil slab, as shown in FIG. 1B. In these implementations, establishing the total heat flux necessitates the summation of dT/dz at both boundaries: top and bottom.

After the heat flux is calculated, the degradation rate can be estimated from the reaction thermodynamics to establish the thermal-gradient based LNAPL losses (Loss). In various circumstances, thermal fluxes can be located at any plane perpendicular to the reactive zone being analyzed. To provide sensitivity analysis to this location, three vertical locations that correspond to the geochemical zones considered above were chosen: the entire vadose zone (between ground level and the groundwater interface—$Loss_{TG,VZ}$); the methane oxidation zone ($Loss_{TG,MOx}$); and the aerobic zone ($Loss_{TG,AE}$), defined between ground level and the bottom of the methane oxidation zone (as shown for example in FIG. 2C).

III. Results

Figure 4:
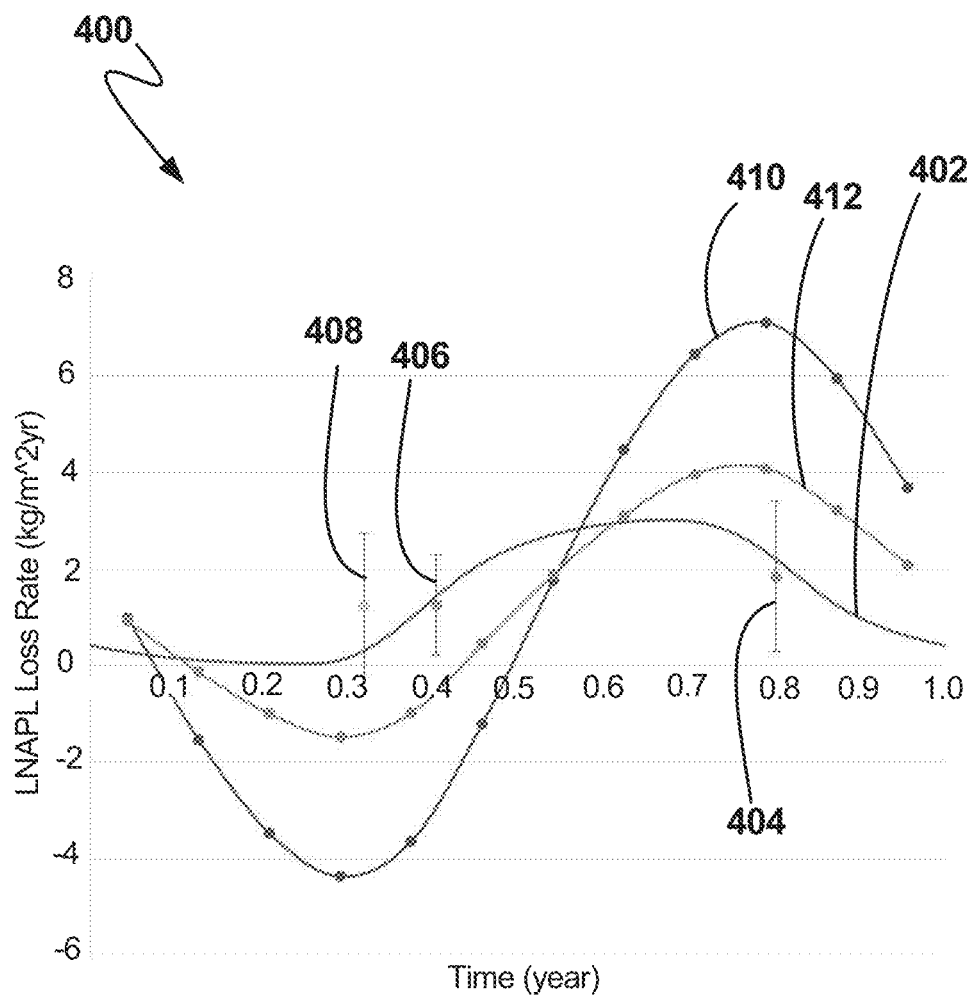
FIG. 4 shows LNAPL loss estimations for the former refinery site, compared to model-predicted and field measured LNAPL losses. Aerobic zone boundaries were not evaluated as there was no contaminant in this zone.

FIG. 4 shows estimates of the biodegradation losses 400 at the former refinery site based on the Monod biodegradation kinetics model and thermal gradients assuming an idealized ambient temperature profile corresponding to an annual sine wave. As shown in FIG. 4, the model predicted LNAPL loss rates from biodegradation kinetics (Eq. 20, $LNAPL_{bio}$) 402 were compared against 3 measured field events 404, 406, 408. FIG. 4 demonstrates the relatively large propensity for error in estimates based on short term thermal gradients at two different locations: the vadose boundary 410 (blue) and the oxidation boundary 412 (green) compared to the model-predicted LNAPL loss rates from biodegradation kinetics ($LNAPL_{bio}$) 402. Accordingly, comparison with the model ($LNAPL_{bio}$) indicates that using raw temperature gradients to estimate the rate of LNAPL biodegradation is subject to large error due to interference from surface and groundwater temperatures. Although the magnitude of the error seems to vary seasonally, timing such a period without the actual biodegradation rates would be difficult. Finally, it was observed that the error seems to be larger in the site with significant aerobic biodegradation, where thermal gradients are even more sensitive to the location.

FIG. 4 therefore shows that although thermal gradient-based reaction rate estimates have a large error rate, these estimates seem to oscillate around the correct mean of the model-based degradation rates. Because the heat propagation process requires time and is prone to a time delay, and that the soil temperatures follow an annual cycle, the long-term calculation of the heat flux based on continuous data through the monitoring locations is able to offer a rigorous estimation of the heat gained and lost through those locations. As the soil temperatures are similar between the beginning and end of the cycles, the net heat gain or loss during this period is negligible.

Figure 5:
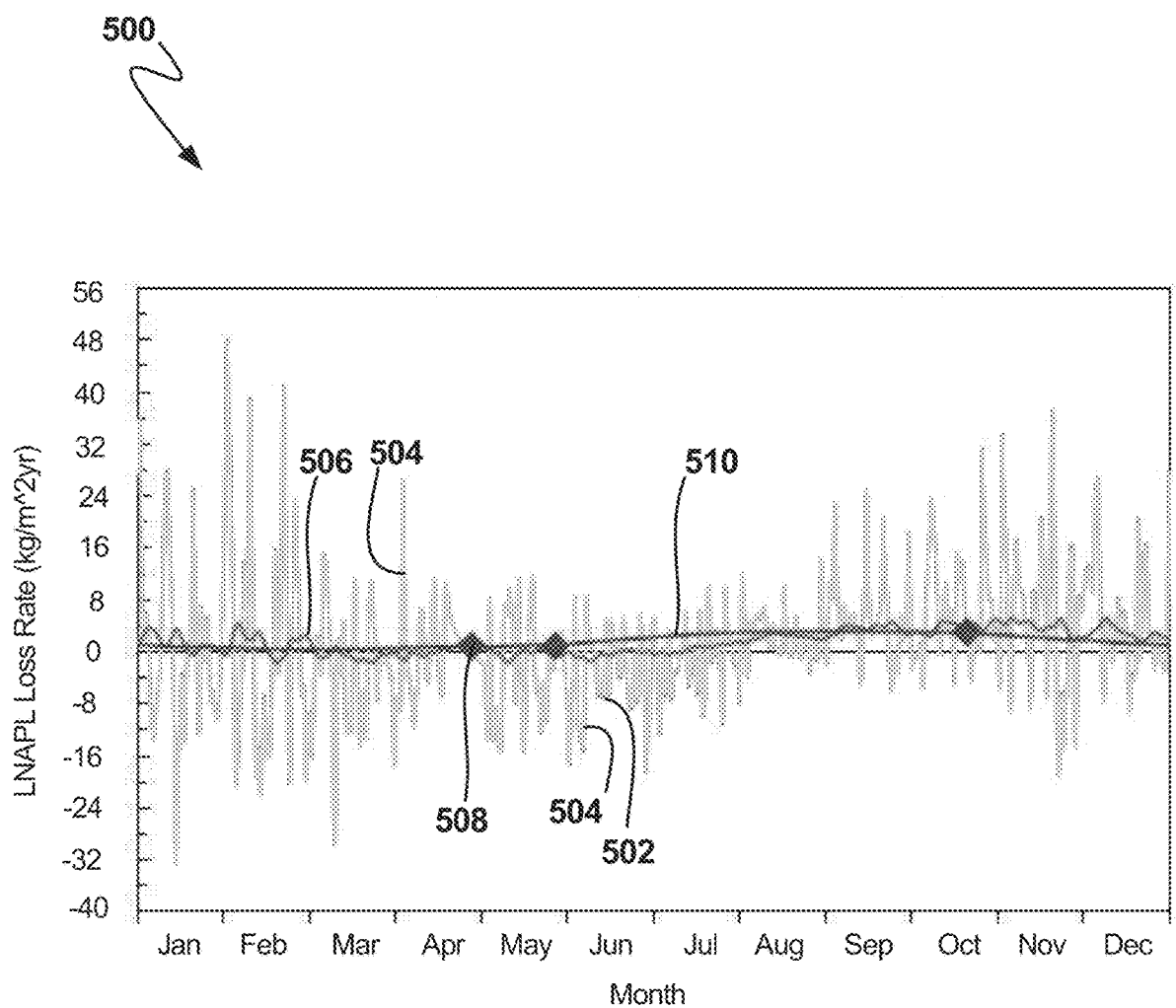
FIG. 5 shows LNAPL loss estimations for the former refinery site, compared to model-predicted and field measured LNAPL losses, using daily ambient temperatures from a nearby weather station. Results for thermal gradient based contaminant losses on aerobic zone were evaluated, but overlap those of the vadose zone.

In FIG. 5, the LNAPL loss estimates 500 were calculated in a similar fashion to those in FIG. 4, however, these estimates assumed daily measured 508 ambient temperatures at a nearby weather station. In FIG. 5, $Loss_{TG,MOx}$ (506), $Loss_{TG,AE}$ (504), and $Loss_{TG,VZ}$ (502), are the biodegradation rate estimates from thermal gradients under the present system 10 using the methane oxidation, aerobic zone and vadose zone boundaries, respectively. As shown in FIG. 5, under short term—here daily—variability, FIG. 5 shows that the error of single time point estimates of the thermal gradient based degradation rates can also be very large.

However, to validate the temporal cycle system 10 heat flux calculation on continuous data, Table 1 shows the average annual calculation of degradation rates. Again, the three locations ($Loss_{TG,MOx}$, $Loss_{TG,AE}$, and $Loss_{TG,VZ}$) are the methane oxidation zone, the aerobic zone, and the entire vadose zone, however, these estimates were compiled over the course of annual data. The $Loss_{TG,MOx}$ estimates based on the methane oxidation zone are within 6% of the Monod-based biodegradation kinetics target, while the vadose zone $Loss_{TG,VZ}$ and aerobic zone $Loss_{TG,AE}$ are within 2% or less. Thus, the system 10 is robust to the selection of monitoring locations when scaled annually, as described above.

TABLE 1

Annual Average LNAPL Losses (Former Refinery)

| | Average Annual LNAPL Loss | |
|---|---|---|
| Soil Zone | Value (kg/m²yr) | Difference from LNAPL$_{bio}$ |
| LOSS$_{TG, MOx}$ | 1.60 | 6.1% |
| LOSS$_{TG, AE}$ | 1.67 | 2.1% |
| LOSS$_{TG, VZ,}$ | 1.68 | 1.5% |

In Table 1, the model-predicted annual average biodegradation losses (LNAPL$_{bio}$—shown in FIG. 5 at 510) were 1.70 kg/m² yr. $Loss_{TG,MOx}$, $Loss_{TG,AE}$, and $Loss_{TG,VZ}$, are the biodegradation rates estimates of the system 10 from thermal gradients using the methane oxidation ($Loss_{TG,MOx}$), aerobic zone ($Loss_{TG,AE}$) and vadose zone ($Loss_{TG,VZ}$) boundaries, respectively.

Example 2: National Crude Oil Research Site, Bemidji MN

In 1979, a pipeline north of Bemidji, MN burst and spilled nearly 10,700 barrels of crude oil that eventually reached the groundwater, where it has since been a source of contamination. Interference of the pipelines with the temperature profile was considered negligible due to their distance (~20 feet) away from the modeled location. Oil saturations along the source zone transect of the north pool oil body for well 9015 were transformed to hydrocarbon concentrations assuming a porosity of 38% and oil density of 777 kg/m³ (for heptadecane). The methane oxidation zone (located 1-2 m below ground) was determined from both soil methane and oxygen concentration data and modeling results. The glacial outwash deposits on the Bemidji site have been classified as sandy gravel to gravelly sand with an average residual water saturation around 15%, resulting in a k=0.7 J/m·k·s. Equations 2 and 22 were used to calculate a=3.58*10_$^{-7}$ m²/s. The daily boundary conditions from surface and groundwater temperatures used as model inputs were available from reported data: a) median surface temperatures were from NOAA station GHCND:US0000MBEM for 2012 (distant about 10 mi E from Well 9015) b) 2012 calendar year groundwater temperature for well 9015 (USGS, 2014, online database).

Heptadecane ($C_{17}H_{36}$) was chosen as the characteristic hydrocarbon for the Bemidji site, consistent with site-specific analysis of the products identified in the source zone. The reactions and their respective heats are shown below. Similarly than for octane, the heat of reaction from methane oxidation heat also represents 98% of the heat of the heat of combustion.

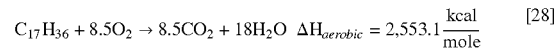

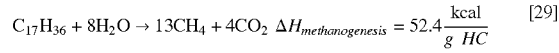

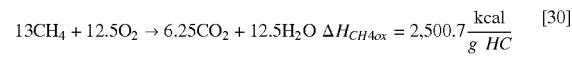

The same values for $k_0$ and $C_m$ used for the former refinery site (for octane, $C_8H_{18}$) were used for heptadecane degradation on the Bemidji site due to lack of specific Monod kinetic parameters for heavy hydrocarbons.

I. Model Solution, Validation, and Calibration

In order to calibrate the model for the former refinery and Bemidji sites, zero-order rates from in situ soil microcosm experiments were adjusted so that model outputs of LNAPL concentration loss matched field estimates of LNAPL loss from $CO_2$ fluxes. Six estimates for NSZD rates on the Bemidji site were available for a location near well 9015 over a 1 year calendar year period (based on $CO_2$ flux corrected for natural soil respiration measured at a nearby background location). Expressed as a multiplier of the lab microcosm data, field zero-order rates fitted in this manner were 0.38 for the Bemidji site. The higher biodegradability observed for Example 1 (the former refinery, characterized by the lower molecular weight octane), with a multiplier of 1.3, is consistent, as smaller molecules are known to be more biodegradable.

II. Results

Figure 6:
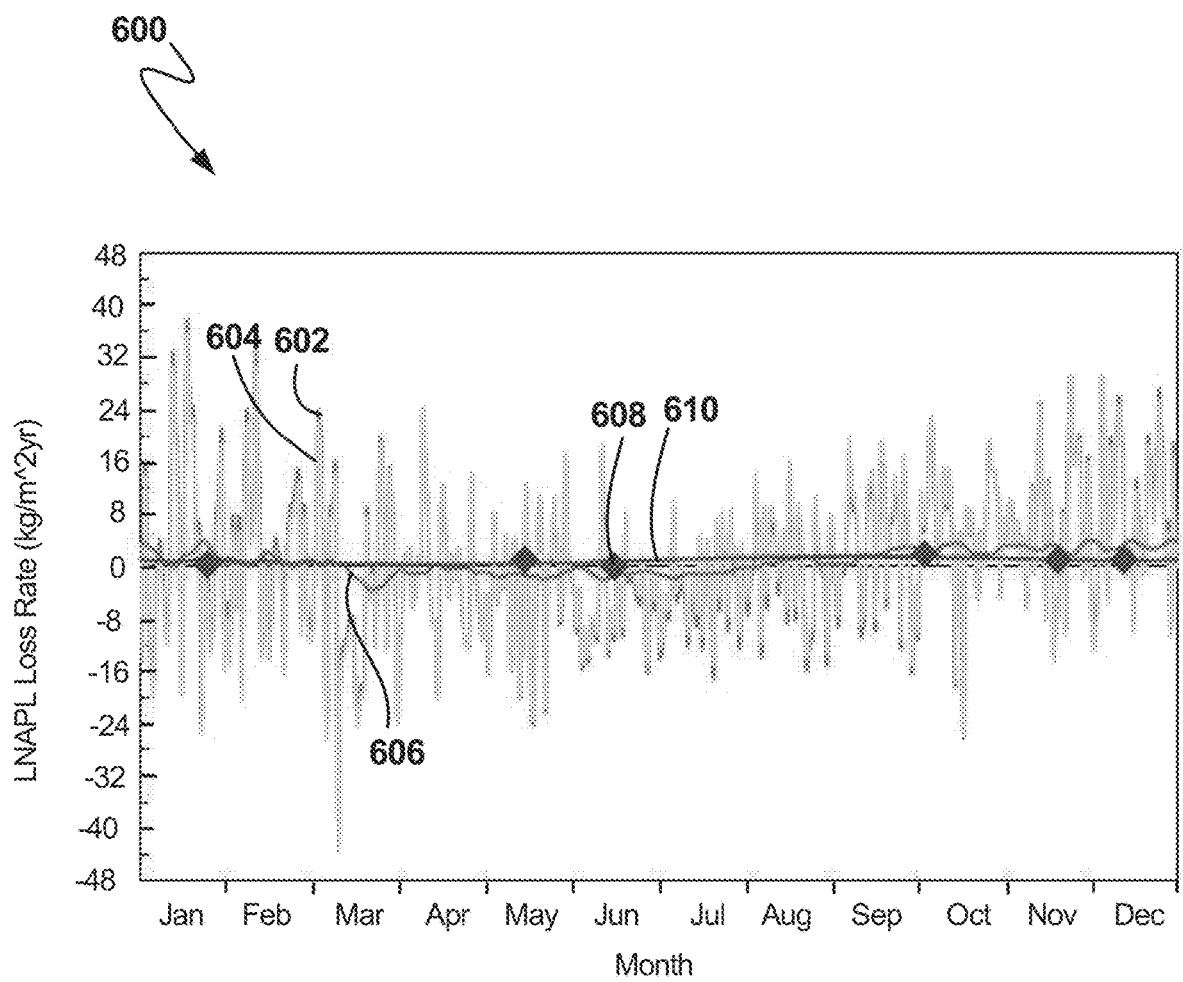
FIG. 6. shows LNAPL loss estimations for the Bemidji site, compared to model-predicted and field measured LNAPL losses, using daily ambient temperatures from a nearby weather station.

Assuming daily measured ambient temperatures at a nearby weather station, FIG. 6 shows estimates 600 of the biodegradation losses ($Loss_{TG,VZ}$ 602, $Loss_{TG,AE}$ 604, and $Loss_{TG,MOx}$ 606) at the Bemidji site based on the Monod biodegradation kinetics model, and based on thermal gradients. The model-predicted LNAPL loss rates from biodegradation kinetics (LNAPL$_{bio}$—610) were calibrated against six measured events 608. FIG. 6 illustrates the large error on the estimates based on thermal gradients at three different locations (green, blue, and gray lines) compared to the Monod-based target estimates (red line).

An implementation of the system 10 to calculate the long term reaction rates based on continuous measurements is shown in Table 2. Applied to two of the three locations (vadose zone and aerobic zone), the system 10 results in an estimation of biodegradation rates within less than 1.5% of the target Monod-based biodegradation rates. The third location (the methane oxidation zone) results in larger error (18.9%) because these limits do not encompass the whole reactive zone (which in this case includes shallow locations where the contaminant is subject to aerobic conditions and thus undergoes degradation). As in the Example 1 (the former refinery) the method proposed is robust to the selection of monitoring locations, as long as they include the zones where heat is released. Although in this case two different reactions occur within the reactive zone (aerobic petroleum degradation and methane oxidation), the heat from both reactions is similar, such as within about 2%. Thus, not knowing the extent of each of these two degradation pathways does not introduce significant error in the calculation.

Previously, a method consisting of using a correction based on the difference between the contaminant-impacted location and an unimpacted (background) location has been proposed. This method has been called the background correction. It has been applied to discreet, single time soil temperature profiles. The results of such background correction in combination with the method proposed here are shown in Table 2. It can be seen that application of the background correction in addition to the method proposed here does not improve the biodegradation rate estimates, which would be nearly impossible to replicate in ongoing field studies.

TABLE 2

Annual Average LNAPL Losses at the Bemidji site.

| Soil Zone | Average Annual LNAPL Loss | | Annual Average Background Corr. LNAPL Loss | |
|---|---|---|---|---|
| | Value (kg/m²yr) | Difference from $LNAPL_{bio}$ | Value (kg/m²yr) | Difference from $LNAPL_{bio}$ |
| $LOSS_{TG, MOx}$ | 0.79 | 18.9% | 0.79 | 19.0% |
| $LOSS_{TG, AE}$ | 0.96 | 1.5% | 0.96 | 1.5% |
| $LOSS_{TG, VZ}$ | 0.97 | 0.1% | 0.97 | 0.1% |

In Table 2, the model-predicted annual average biodegradation losses ($LNAPL_{bio}$) were 0.97 kg/m² y. $Loss_{TG,MOx}$, $Loss_{TG,AE}$ and $Loss_{TG,VZ}$, are the biodegradation rates estimates of the system 10 from thermal gradients using the methane oxidation ($Loss_{TG,MOx}$), aerobic zone ($Loss_{TG,AE}$) and vadose zone ($Loss_{TG,VZ}$) boundaries, respectively.

CONCLUSIONS

Temporal soil temperatures trends at both relatively shallow, cold weather sites studied suggest that thermal regimes in the subsurface change on a seasonal basis, and are controlled to a large degree by surface and groundwater temperatures. Model predicted temperatures within the soil confirm empirical field observations that biodegradation rates at contaminated sites might be seasonal, with maximum rates towards the late summer/early fall and minimal during the winter. Thus, field measurements of long term biodegradation rates need to account for such seasonal variability.

The model validates that the presently disclosed system represents significant improvements in the art. In a prior art study invoking discrete soil temperature measurements in Sweeney, R. E., and Ririe G. T., Temperature as a Tool to Evaluate Aerobic Biodegradation in Hydrocarbon Contaminated Soil. Ground Water Monitoring and Remediation. 34:41-50. doi:10.1111/gwmr.12064 (2014)("Sweeney") were taken by lowering a sensor into an existing well. Such data collection method introduces large errors, as the existing well acts as a mixing cell, resulting in the well void having different temperatures than the surrounding soil. The procedure used by Sweeney consists of taking a single reading of temperature profiles within a well to establish the T(z) data series as the basis for the thermal gradient and heat flux. The background correction was implemented by repeating the procedure at an unimpacted location, with the difference in temperatures at impacted and background correction used to determine the background corrected heat flux due to biodegradation reactions.

Figure 7:
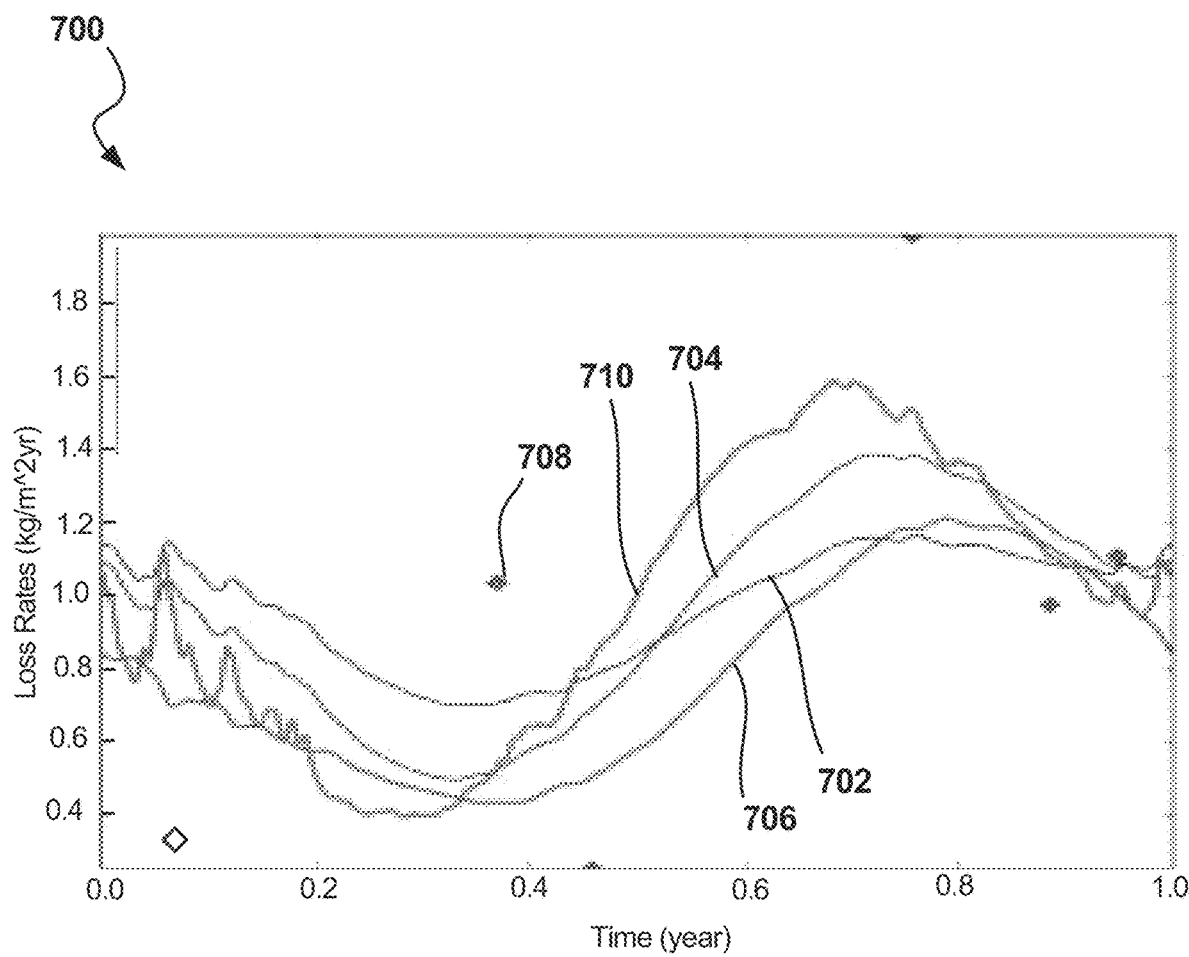
FIG. 7. shows background corrected estimated and model-predicted LNAPL loss rates for Bemidj using daily ambient temperatures from a nearby weather station.

FIG. 7 depicts background corrected estimated and modeled LNAPL loss rates for Bemidji using daily ambient temperatures measured 708 from a nearby weather station. In FIG. 7, these $LNAPL_{Loss}$ rates 700 are shown, including $Loss_{TG,VZ}$ 702, $Loss_{TG,AE}$ 704, $Loss_{TG,MO}$ 706, and $LNAPL_{Bio}$ 710.

Figure 8:
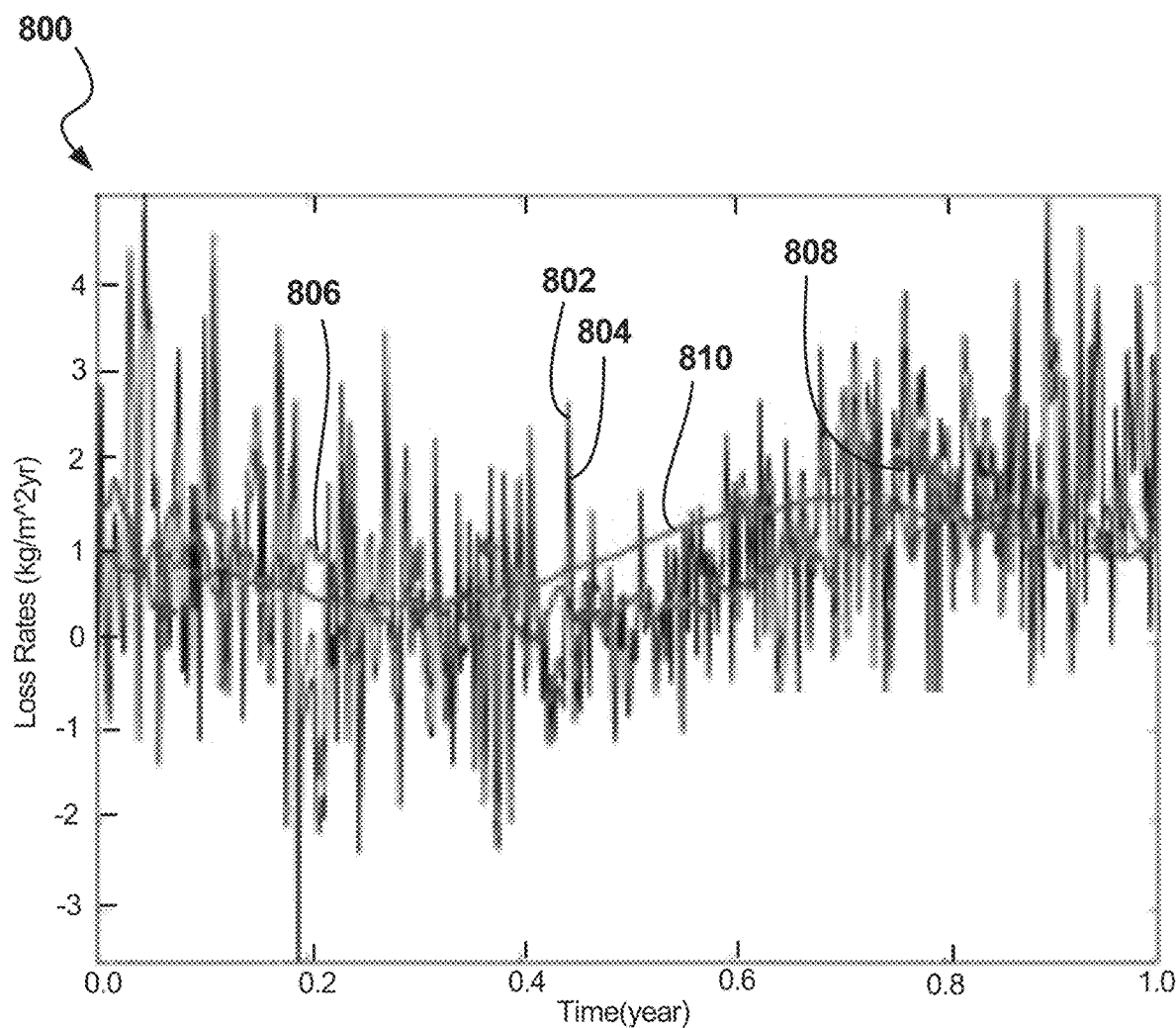
FIG. 8 shows background corrected estimated and model-predicted LNAPL loss rates for Bemidji LNAPL loss estimations for the Bemidji site, compared to model-predicted and field measured LNAPL losses, using daily ambient temperatures from a nearby weather station. The background correction was done by assuming the background location to have a different thermal conductivity (k=0.8 J/m/K/s instead of k=0.7 J/m/K/s for the reactive zone).

FIG. 8 depicts background corrected estimated and model-predicted LNAPL loss rates for Bemidji 800 $Loss_{TG,VZ}$ 802, $Loss_{TG,AE}$ 804, $Loss_{TG,MO}$ 8, from measured sites 808, as well as $LNAPL_{Bio}$ 810. LNAPL loss estimations for the Bemidji site, compared to model-predicted and field measured LNAPL losses, using daily ambient temperatures from a nearby weather station. The background correction was done by assuming the background location to have a different thermal conductivity (k=0.8 J/m/K/s instead of k=0.7 J/m/K/s for the reactive zone).

The present system differs in several important ways. First, the Sweeney procedure only uses one specific reaction: the aerobic degradation of petroleum. It does not apply to the anaerobic degradation of petroleum as in the invention, which applies to multiple mechanisms. Second, the Sweeney procedure to estimate aerobic biodegradation is acknowledged by Sweeney as semiquantitative by indicating it is a minimum rate or a relative rate. The Sweeney procedure is described as one to determine reaction rates at discrete times. The present system 10 on the contrary measures the long-term average (time integrated) degradation rate, as it is acknowledged that the discrete calculation has a large error rate, even with the background correction. Third, the Sweeney procedure requires a background correction. The present system does not require a background correction, as the error introduced by short-term measurements is dealt with by performing measurements over a large time scale. Finally, Sweeny teaches the use of a constant heat conductivity, while the present system 10 does not.

The model was useful for distinguishing soil heat generated from biodegradation of petroleum hydrocarbons versus the noise due to variable groundwater and ambient temperatures. Thus, estimating the rate of contaminant biodegradation by measuring thermal gradient-based heat fluxes in the soil is promising. Soil temperature measurements are relatively inexpensive and easy to obtain year round, making thermal gradients useful for monitoring NSZD. Methods presented in this paper have the potential to estimate NSZD rates at sites where other methods are difficult to implement.

The model enabled identification of the following lessons toward the implementation of such methodology.

Thermal processes in the soil are complex, as boundary conditions from groundwater and ambient temperatures change, and there is a time delay for the heat generated by reactions within the soil to locations where the thermal gradients are measured. Thus, the model suggests that single time raw thermal gradients (without correction) proved to be subject to high error in making an adequate estimate of single time biodegradation rates based on heat fluxes.

Both of the two corrections to the raw thermal gradients tested in this work, background correction and long term time integration significantly improved the estimate of biodegradation losses based on thermal gradients. Both corrections can be used in combination.

Averaging thermal fluxes over a full seasonal cycle showed to be the most effective single correction to estimate long-term annual biodegradation rates. When compared to the target values from model-predicted biodegradation rates based on Monod biodegradation kinetics, the annual average was within 3% of the target for the former refinery site, and 2% of the target for the Bemidji site when considering the aerobic and vadose zone boundaries. When thermal gradient locations were chosen at the methane oxidation zone (not including the full reactive zone at the Bemidji site, which has a distinct aerobic zone), the error increased to 19% difference from the target. This highlights the importance of choosing the thermal gradient locations outside of the biologically reactive zone.

The background correction alone was able to provide single time estimates within approximately ±10% of the target values for the site without an aerobic zone for the full year, and within about 30% for the Bemidji site. As in the case of the long term average thermal fluxes, selection of the thermal gradient boundaries within the reactive zone (the methane oxidation zone in the Bemidji site) and far from the location of heat generation (the vadose zone on the Bemidji site) generated significant error in LNAPL loss estimation. Choosing boundaries that encompass the majority of the heat generated while being close to the source (i.e. the aerobic zone on Bemidji) produces the closest LNAPL loss estimation to the target.

It is noted that for the background correction, both contaminated and background locations were identical (except for the presence of contaminant). A practical limitation is that such condition would be difficult to replicate in the field, as it is subject to site heterogeneity or local conditions, even if a contaminant-free background location were available. For example, previous work suggests that contaminated locations have higher groundwater temperatures which may be affected by cumulative upstream thermal effects due to contaminant degradation. Parametric sensitivity analysis indicated that a small difference in properties such as about 3% in soil moisture between background location and an impacted location (other than the presence of contaminant) can led to error rates in the order of 300%.

When used in combination, the background correction did not improve estimates based on annual long term thermal fluxes. These results imply that a background correction is not needed for estimation of a long term, cyclic or temporal average LNAPL loss rate, although it can be used in combination if single time estimates throughout the year are desired. Not having to use a background location decreases the chance for error from using an imperfect background location.

As used herein, the terms "optional" or "optionally" mean that the subsequently described event or circumstance can or cannot occur, and that the description includes instances where said event or circumstance occurs and instances where it does not.

As used herein, ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

Although the disclosure has been described with reference to preferred embodiments, persons skilled in the art will recognize that changes may be made in form and detail without departing from the spirit and scope of the disclosed apparatus, systems and methods.

What is claimed is:

1. A system for establishing a rate of contaminant biodegradation in a reactive zone having a soil volume, comprising:
   a. at least two temperature sensors configured to continuously record soil data of the reactive zone;
   b. a database, in communication with the at least two temperature sensors, the database configured to store the soil data;
   c. a central processor in communication with the database; and
   d. a storage device comprising reaction rate estimation software,
   wherein the reaction rate estimation software is configured to calculate, from the soil data, the rate of contaminant biodegradation by establishing:
      i. temperature gradients of the reactive zone and
      ii. time integrated thermal heat flux of the reactive zone over an annual or a seasonal cycle.

2. The system of claim 1, wherein the reaction rate estimation software is configured to model at least one of the group of consisting of: contaminant degradation reactions, methanogenic petroleum degradation, methane oxidation or aerobic petroleum biodegradation.

3. The system of claim 1, wherein the reaction rate estimation software is configured to establish a biodegradation rate per unit of soil in the soil reactive zone.

4. The system of claim 1, wherein the reaction rate estimation software is configured to report groundwater heat loss or gains from exothermic soil reactions.

5. The system of claim 1, wherein the reaction rate estimation software is configured to report the biodegradation rate without performing a background correction.

6. The system of claim 1, wherein the reaction rate estimation software is configured process at least one of the group consisting of: contaminant biodegradation rates, contaminant distribution, soil properties, ambient temperatures, groundwater temperatures, and combinations thereof.

7. The system of claim 1, wherein the reaction rate estimation software is configured to validate a perimeter of the reactive zone.

8. The system of claim 1, wherein the reaction rate estimation software is configured to validate the rate of contaminant biodegradation against a biodegradation model.

9. A method of measuring a rate of an exothermic reaction in soil having at least one organic contaminant or contaminant reaction-intermediate, the method comprising:
   a. defining a reactive zone perimeter having an outside and an inside comprising a soil volume containing the at least one organic contaminant or contaminant reaction-intermediate;
   b. emplacing at least two temperature measurement devices at the reactive zone perimeter;
   c. recording, by a processor, soil data at each of the temperature measurement devices, on a database configured to compile soil data;
   d. calculating, on the processor, at least one thermal gradient from the soil data from each of the temperature measurement devices;
   e. establishing, on the processor, time integrated heat flux at the reactive zone perimeter by calculating, from the soil data, heat flux over time; and
   f. determining, on the processor, an exothermic reaction rate of the contaminant or contaminant reaction-intermediate over an annual or a seasonal cycle.

10. The method of claim 9, wherein the processor is configured process at least one of the group consisting of: contaminant biodegradation rates, contaminant distribution, soil properties, ambient temperatures, groundwater temperatures, and combinations thereof.

11. The method of claim 9, wherein the exothermic reaction in the soil consists of at least one of the group consisting of: methanogenic petroleum biodegradation, methane oxidation or aerobic petroleum biodegradation.

12. The method of claim 9, further comprising evaluating seasonal dependence of the exothermic reaction due to variable ambient temperatures.

13. The method of claim 9, further comprising establishing a biodegradation rate per unit of soil in the reactive zone.

14. The method of claim 9, further comprising reporting groundwater heat loss or gains from the exothermic reaction.

* * * * *